US012193725B2

(12) United States Patent
Hughett, Sr. et al.

(10) Patent No.: US 12,193,725 B2
(45) Date of Patent: *Jan. 14, 2025

(54) SURGICAL CLAMP

(71) Applicant: AtriCure, Inc., Mason, OH (US)

(72) Inventors: James David Hughett, Sr., Monroe, GA (US); Salvatore Privitera, Mason, OH (US)

(73) Assignee: AtriCure, Inc., Mason, OH (US)

(*) Notice: Subject to any disclaimer, the term of this patent is extended or adjusted under 35 U.S.C. 154(b) by 327 days.

This patent is subject to a terminal disclaimer.

(21) Appl. No.: 17/567,485

(22) Filed: Jan. 3, 2022

(65) Prior Publication Data
US 2022/0117653 A1    Apr. 21, 2022

Related U.S. Application Data

(63) Continuation of application No. 16/582,564, filed on Sep. 25, 2019, now Pat. No. 11,241,276, which is a continuation of application No. 14/529,822, filed on Oct. 31, 2014, now Pat. No. 10,492,851, which is a continuation of application No. 12/748,842, filed on Mar. 29, 2010, now Pat. No. 8,876,820.

(51) Int. Cl.
A61B 18/00   (2006.01)
A61B 17/29   (2006.01)
A61B 18/14   (2006.01)

(52) U.S. Cl.
CPC .......... *A61B 18/1445* (2013.01); *A61B 17/29* (2013.01); *A61B 18/1447* (2013.01); *A61B 2017/2927* (2013.01); *A61B 2017/2944* (2013.01); *A61B 2017/2945* (2013.01); *A61B 2018/00577* (2013.01); *A61B 2018/1432* (2013.01)

(58) Field of Classification Search
CPC .................................. A61B 18/1445
USPC ......................................... 606/41
See application file for complete search history.

(56) References Cited

U.S. PATENT DOCUMENTS

2009/0018535 A1* 1/2009 Schechter .......... A61B 18/1445
                                                           606/41
2009/0187185 A1* 7/2009 Lyons ................ A61B 17/2909
                                                           606/41
2010/0185232 A1* 7/2010 Hughett, Sr. ...... A61B 18/1445
                                                           606/205

* cited by examiner

*Primary Examiner* — Nicole F Lavert
(74) *Attorney, Agent, or Firm* — Dorton & Willis LLP; Ryan Willis

(57) ABSTRACT

A surgical clamp including a pair of jaws, which may be used to ablate or create lesions in tissue. In an exemplary embodiment, the jaws are movable between an articulated position in which the jaws are separated and not parallel to one another, an opened position in which the jaws are separated and substantially parallel to one another, and a closed position in which the jaws are adjacent and substantially parallel to one another.

19 Claims, 27 Drawing Sheets

SURGICAL CLAMP

CROSS REFERENCE TO RELATED APPLICATIONS

This application is a continuation of U.S. Nonprovisional application Ser. No. 16/582,564, filed Sep. 25, 2019, now U.S. Pat. No. 11,241,276, which is a continuation of U.S. Nonprovisional application Ser. No. 14/529,822, filed Oct. 31, 2014, now U.S. Pat. No. 10,492,851, which is a continuation of U.S. Nonprovisional application Ser. No. 12/748,842, filed Mar. 29, 2010, now U.S. Pat. No. 8,876,820, all of which are incorporated herein by reference.

RELATED ART

The present disclosure relates to surgical instruments, with some embodiments relating to clamps, articulated clamps, and/or tissue ablating clamps. Surgery and surgical procedures generally refer to the diagnosis or treatment of injury, deformity, or disease. In a variety of surgical procedures, it is desired to ablate tissue and/or cause lesions in tissue. Some examples of such procedures include, without limitation, electrical isolation of the pulmonary veins to treat atrial fibrillation, ablation of uterine tissue associated with endometriosis, ablation of esophageal tissue associated with Barrett's esophagus, ablation of cancerous liver tissue, and the like. The foregoing examples are merely illustrative and not exhaustive. Other aspects of the present disclosure relate to clamping devices and are not limited to tissue ablation applications.

INTRODUCTION TO THE INVENTION

Some exemplary embodiments according to the present disclosure may include surgical clamps including a pair of jaws, which may be used to ablate or create lesions in tissue. In an exemplary embodiment, the jaws may be movable between an articulated position in which the jaws are separated and not parallel to one another, an opened position in which the jaws are separated and substantially parallel to one another, and a closed position in which the jaws are adjacent and substantially parallel to one another.

In an exemplary aspect, a surgical clamp may include an end effector including a first jaw, a second jaw, and a head including an articulating mechanism, the articulating mechanism including a first rotating offset mounted to the head and pivotably coupled to the first jaw, and a second rotating offset mounted to the head distal from the first rotating offset and pivotably and slidably coupled to the first jaw. The articulating mechanism may articulate the first jaw when the first rotating offset and the second rotating offset are rotated.

In a detailed exemplary embodiment, a surgical clamp may include a rack operably coupled to a distally extending linkage, the first rotating offset may include a first gear, and the second rotating offset may include a second gear. The rack may be toothedly engaged with the first gear and the second gear and/or the articulating mechanism may articulate the first jaw when the rack is moved by the linkage.

In a detailed exemplary embodiment, an articulating mechanism may include a third gear rotatably mounted to the head, engaged with the rack, and pivotably coupled to the second jaw, and a fourth gear rotatably mounted to the head, engaged with the rack, and pivotably and slidably coupled to the second jaw. The articulating mechanism may articulate the second jaw when the rack is moved by the linkage and/or the rack may be double-sided.

In a detailed exemplary embodiment, a surgical clamp may include a first cable operably coupled to a distally extending linkage, the first rotating offset may include a first pulley operatively engaged with the cable, and the second rotating offset may include a second pulley operatively engaged with the cable. The articulating mechanism may articulate the first jaw when the cable is moved by the linkage.

In a detailed exemplary embodiment, an articulating mechanism may include a third pulley rotatably mounted to the head, engaged with a second cable, and pivotably coupled to the second jaw, and a fourth pulley rotatably mounted to the head, engaged with the second cable, and pivotably and slidably coupled to the second jaw. The articulating mechanism may articulate the second jaw when the second cable is moved by the linkage.

In a detailed exemplary embodiment, the first cable may extend distally around the second pulley, proximally around the first pulley, and/or distally around the second pulley. The second cable may extend distally around the fourth pulley, proximally around the third pulley, and/or distally around the fourth pulley.

In a detailed exemplary embodiment, the first cable may include a continuous section of cable operatively engaging the first pulley and the second pulley. In a detailed embodiment, the first cable may include wire rope.

In a detailed exemplary embodiment, the first jaw and the second jaw may be articulatable by the articulating mechanism between an articulated position in which the first jaw and the second jaw are spaced apart with respect to each other at the head and are angled outwardly relative to the end effector, an opened position in which the first jaw and the second jaw are spaced apart with respect to each other at the head and are substantially parallel such that target tissue interposes the substantially parallel first jaw and second jaw, and a closed position in which the first jaw and the second jaw close on the target tissue while remaining substantially parallel.

In a detailed exemplary embodiment, in the closed position when empty, the first jaw and the second jaw may be biased inward from parallel and/or, when interposed by the target tissue, the first jaw and the second jaw may be substantially parallel in the closed position. In a detailed embodiment, in the closed position when empty, the first jaw and the second jaw may be biased inward about 0.010-0.040 inches. In a detailed exemplary embodiment, in the articulated position, the first jaw may be angled with respect to the second jaw at about 20 degrees. In a detailed exemplary embodiment, in at least one of the opened position and the closed position, the first jaw may be substantially parallel with the second jaw within about +/−5 degrees. In a detailed exemplary embodiment, in at least one of the opened position and the closed position, the first jaw may be substantially parallel with the second jaw within about +/−3 degrees. In a detailed exemplary embodiment, in at least one of the opened position and the closed position, the first jaw may be substantially parallel with the second jaw within about +/−0.5 degrees.

In a detailed exemplary embodiment, a surgical clamp may include at least one electrode associated with at least one of the first jaw and the second jaw. In a detailed exemplary embodiment, the first jaw and the second jaw may extend generally distally from the head generally in a Y-shape or a V-shape.

In a detailed exemplary embodiment, a surgical clamp may include a shaft including a proximal end and a distal end, and the end effector may be mounted approximate the distal end of the shaft. In a detailed exemplary embodiment, a surgical clamp may include a handle at the proximal end of the shaft. In a detailed exemplary embodiment, a surgical clamp may include a linkage extending from the handle, through the shaft, and to the end effector. The handle may include a plunger operatively coupled to the linkage such that actuation of the plunger causes articulation of the first jaw. In a detailed exemplary embodiment, a surgical clamp may include a reversing mechanism interposing the plunger and the linkage such that motion of the plunger in a first direction causes motion of the linkage in a substantially opposite direction. In a detailed exemplary embodiment, a reversing mechanism may include a plunger rack extending distally from the plunger and/or a linkage rack extending proximally from the linkage.

In a detailed exemplary embodiment, the end effector may be mounted to the distal end of the shaft by at least one articulating joint such that the articulating joint allows pivoting of the end effector with respect to the shaft. In a detailed exemplary embodiment, the shaft may be substantially rigid. In a detailed exemplary embodiment, the shaft may be substantially malleable.

In an exemplary aspect, a surgical clamp may include an end effector including a first rotating offset, a second rotating offset, a first jaw mounted to the first rotating offset and the second rotating offset, a third rotating offset, a fourth rotating offset, and a second jaw mounted to the third rotating offset and the fourth rotating offset.

In a detailed exemplary embodiment, the first rotating offset may be pivotably coupled to the first jaw by a first pin, the second rotating offset may be pivotably and/or slidably coupled to the first jaw by a second pin slidable in a first slot, the third rotating offset may be pivotably coupled to the second jaw by a third pin, and/or the fourth rotating offset may be pivotably and/or slidably coupled to the second jaw by fourth pin slidable in a second slot.

In a detailed exemplary embodiment, the end effector may be configured such that rotation of the first rotating offset and the second rotating offset in a clockwise direction moves the first jaw towards the second jaw and/or rotation of the third rotating offset and the fourth rotating offset in a counter-clockwise direction moves the second jaw towards the first jaw.

In a detailed exemplary embodiment, rotation of the first rotating offset and the second rotating offset in the clockwise direction and rotation of the third rotating offset and the fourth rotating offset in the counter-clockwise direction may move the first jaw and the second jaw from an articulated position in which the first jaw and the second jaw are spaced apart with respect to each other and are angled outwardly relative to the end effector, through an opened position in which the first jaw and the second jaw are spaced apart with respect to each other and are substantially parallel, and to a closed position in which the first jaw and the second jaw close while remaining substantially parallel.

In a detailed exemplary embodiment, movement of the first jaw from the articulated position to the closed position may include rotation of the first jaw relative to the first rotating offset about the first pin, rotation of the first jaw relative to the second rotating offset about the second pin, and/or translation of the second pin in the first slot; and/or movement of the second jaw from the articulated position to the closed position may include rotation of the second jaw relative to the third rotating offset about the third pin, rotation of the second jaw relative to the fourth rotating offset about the fourth pin, and/or translation of the fourth pin in the second slot.

In a detailed exemplary embodiment, a surgical clamp may include a double-sided rack including a first side and a second side. The first rotating offset may include a first gear engaged with the first side of the rack, the second rotating offset may include a second gear engaged with the first side of the rack, the third rotating offset may include a third gear engaged with the second side of the rack, and/or the fourth rotating offset may include a fourth gear engaged with the second side of the rack.

In a detailed exemplary embodiment, a surgical clamp may include a first cable and/or a second cable. The first rotating offset may include a first pulley, the second rotating offset may include a second pulley, the third rotating offset may include a third pulley, and/or the fourth rotating offset may include a fourth pulley. The first cable may be operatively engaged with the first pulley and/or the second pulley. The second cable may be operatively engaged with the third pulley and/or the fourth pulley.

In an exemplary aspect, an end effector for a surgical device may include a pair of jaws including a first jaw and a second jaw; and an articulating mechanism configured to articulate the pair of jaws between an articulated position in which the first jaw and the second jaw are spaced apart with respect to each other and are angled outwardly with respect to each other, an opened position in which the first jaw and the second jaw are spaced apart with respect to each other and substantially parallel such that target tissue interposes the substantially parallel first jaw and second jaw, and a closed position in which the first jaw and the second jaw close on the target tissue while remaining substantially parallel, the articulating mechanism including a first rotating offset coupled to the first jaw, and a second rotating offset coupled to the first jaw. The first rotating offset and/or the second rotating offset may be operatively coupled to a linkage extending generally distally from the end effector.

In a detailed exemplary embodiment, the articulating mechanism may include a third rotating offset coupled to the second jaw and/or a fourth rotating offset coupled to the second jaw. The third rotating offset and/or the fourth rotating offset may be operatively coupled to the linkage.

In a detailed exemplary embodiment, the first rotating offset may be pivotably coupled to the first jaw, the second rotating offset may be pivotably and/or slidably coupled to the first jaw, the third rotating offset may be pivotably coupled to the second jaw, and/or the fourth rotating offset may be pivotably and/or slidably coupled to the second jaw.

In a detailed exemplary embodiment, the first rotating offset may include a first gear and/or the second rotating offset may include a second gear, the first gear and/or the second gear may be in toothed engagement with a first side of a rack, and/or the rack may be operatively connected to the linkage. The third rotating offset may include a third gear and/or the fourth rotating offset may include a fourth gear, and/or the third gear and/or the fourth gear may be in toothed engagement with a second side of the rack.

In a detailed exemplary embodiment, the first rotating offset may include a first pulley, the second rotating offset may include a second pulley, the third rotating offset may include a third pulley, and/or the fourth rotating offset may include a fourth pulley. The first pulley and/or the second pulley may be operatively connected to the linkage by a first cable and/or the third pulley and/or the fourth pulley may be operatively connected to the linkage by a second cable.

In an exemplary aspect, a surgical clamp may include a shaft including a proximal end and a distal end; and an end effector mounted at the distal end of the shaft, the end effector including a first jaw, a second jaw, and a head including an articulating mechanism, the articulating mechanism including a first rotating offset mounted to the head and pivotably coupled to the first jaw by a first pin, and a second rotating offset mounted to the head distal from the first rotating offset and pivotably and slidably coupled to the first jaw distal from the first rotating offset by a second pin slidably disposed in a slot in the first jaw, the second rotating offset having a diameter greater than a diameter of the first rotating offset.

In a detailed exemplary embodiment, the first jaw may be articulatable by the articulating mechanism between an articulated position in which the first jaw is spaced apart from a centerline and is angled outwardly relative to the shaft, an opened position in which the first jaw is spaced apart from the centerline at the head and is substantially parallel with the centerline, and a closed position in which the first jaw is substantially parallel to and substantially adjacent to the centerline.

In a detailed exemplary embodiment, in the articulated position, the second pin may be located near a distal end of the slot; in the opened position, the second pin may be located about mid-way between the distal end of the slot and a proximal end of the slot; and/or, in the closed position, the second pin may be located near a proximal end of the slot.

In a detailed exemplary embodiment, in the articulated position, the first pin may be located at approximately a 5 o'clock position on the first rotating offset and/or the second pin may be located at approximately a 6 o'clock position on the second rotating offset; in the opened position, the first pin may be located at approximately a 7 o'clock position on the first rotating offset and/or the second pin may be located at approximately an 8 o'clock position on the second rotating offset; and/or, in the closed position, the first pin may be located at approximately a 10 o'clock position on the first rotating offset and/or the second pin may be located at approximately a 10 o'clock position on the second rotating offset.

In a detailed exemplary embodiment, the first rotating offset may include a first gear; the second rotating offset may include a second gear; and/or the articulating mechanism may include a rack slidably disposed within the head in toothed engagement with the first gear and the second gear such that translation of the rack in proximal and distal directions causes rotation of the first gear and second gear, thereby causing articulation of the first jaw. In a detailed exemplary embodiment, the rack may be slidably disposed substantially along a centerline of the end effector. In a detailed exemplary embodiment, the first gear and/or the second gear may be mounted to the head such that the rack engages each of the first gear and the second gear at about respective 12 o'clock positions.

In a detailed exemplary embodiment, the first rotating offset may include a first pulley; the second rotating offset may include a second pulley; and/or the articulating mechanism may include a cable disposed at least partially within the head and engaged with the first pulley and the second pulley such that translation of the cable in proximal and distal directions causes rotation of the first pulley and second pulley, thereby causing articulation of the first jaw. In a detailed embodiment, the cable may extend distally around the second pulley, proximally around the first pulley, and/or distally around the second pulley.

BRIEF DESCRIPTION OF THE DRAWINGS

The detailed description refers to the following figures.

DETAILED DESCRIPTION

The following description of exemplary embodiments should not be used to limit the scope of the present disclosure. Other examples, features, aspects, embodiments, and advantages may become apparent to those skilled in the art from the following description. As will be realized, exemplary embodiments may include optional aspects that are not required to fall within the scope of claimed invention. Accordingly, the drawings and descriptions should be regarded as illustrative in nature and not restrictive.

In a variety of surgical procedures, it is desirable to ablate tissue and/or cause lesions in tissue. Tissue ablation can be effected through a variety of different mechanisms known to those of skill in the art, such as mono-polar radiofrequency ("RF") energy, bi-polar RF energy, cryogenic techniques, and the like. In clamping arrangements, tissue ablation can be effected through a single jaw of a clamp or through both jaws of a clamp. Tissue ablation may be performed once the target tissue is clamped between the closed jaws. One with ordinary skill in the art will recognize that one or more of the foregoing tissue ablation techniques may be employed with the various clamp embodiments described below. One with ordinary skill in the art will also recognize advantages of the surgical clamps regardless of any tissue ablation functionality. Accordingly, the foregoing examples may or may not include ablation functionality.

Figure 1:
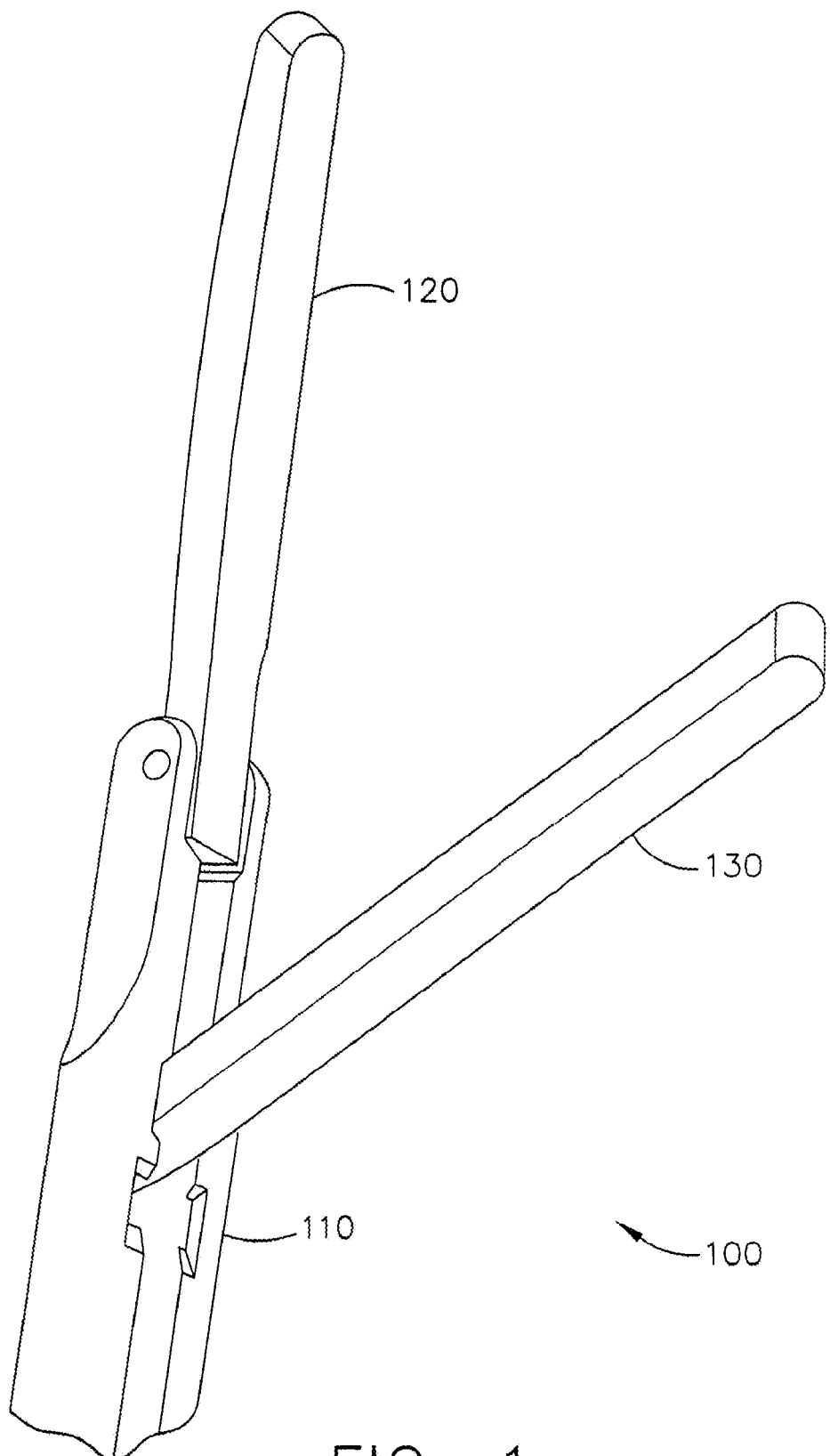
FIG. 1 illustrates an oblique view of an example of an articulated clamp in an articulated position.

FIG. 1 illustrates an example of an articulated clamp 100. The clamp 100 includes a shaft 110, a distal jaw 120, and a proximal jaw 130. The shaft could be one or more of the following: straight, curved, rigid, flexible, malleable, and articulated. In this exemplary embodiment, the jaws are substantially straight; however, the jaws could also be curved in one or more directions. As shown here, the jaws are in an articulated position where the jaws are separated and not parallel to one another. The distal jaw 120 can articulate relative the shaft 110 independent of the proximal jaw 130. As shown here, the distal jaw 120 extends distally relative to the shaft 110 and the proximal jaw 130 extends laterally relative to the shaft 110. Note that the distal jaw 120 need not be axially aligned with the shaft 110, and likewise the proximal jaw 130 need not extend normal to the shaft 110. Instead, angular variations are contemplated, and in many cases may be advantageous based on the anticipated anatomy or surgical procedure contemplated.

Figure 2:
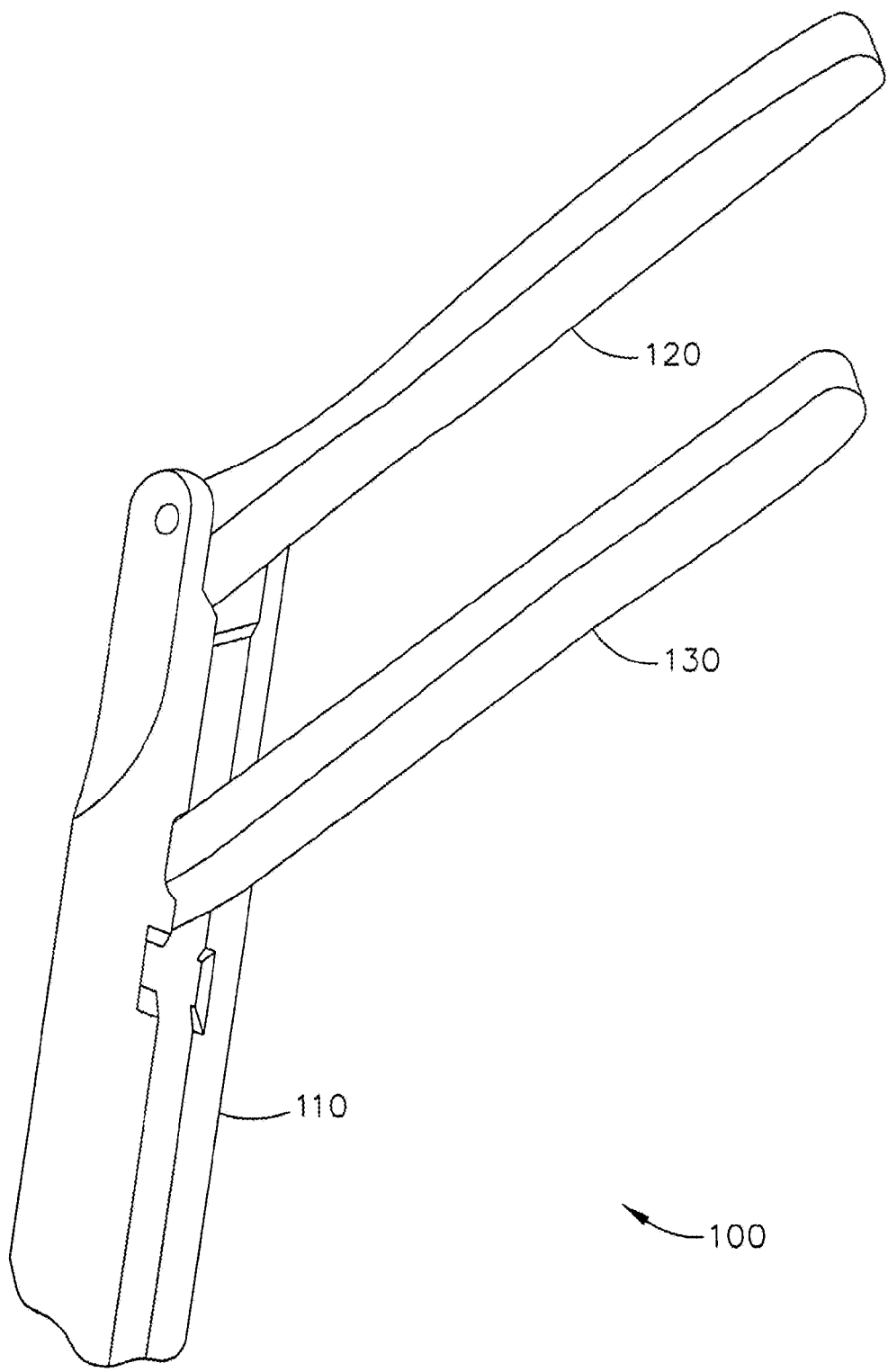
FIG. 2 illustrates an oblique view of the articulated clamp of FIG. 1 in an opened position.

FIG. 2 illustrates the articulate clamp 100 in an opened position where the jaws are separated and substantially parallel to one another. The distal jaw 120 has been articulated such that the distal jaw 120 extends laterally from the shaft 110.

The articulation of the jaws 120, 130 can be passive. For instance, the articulated jaw can be "limp" and readily moveable in response to external forces, such as when pressed against tissue, or resisted by a spring, damper, friction, or other biasing mechanism. Alternatively, the articulation of the jaws 120, 130 could be active in which the articulation is remotely activated through an actuator (not shown), such as one located on the proximal end of the shaft 110. With active articulation, the jaws 120, 130 are generally rigid and immobile in response to external forces. The jaws can move to a closed position where the jaws are adjacent and substantially parallel to one another. As shown in this example, one or both of the jaws 120, 130 are repositionable axially relative to the shaft 110 so that the jaws remain parallel to one another between the opened and closed positions.

Figure 3:
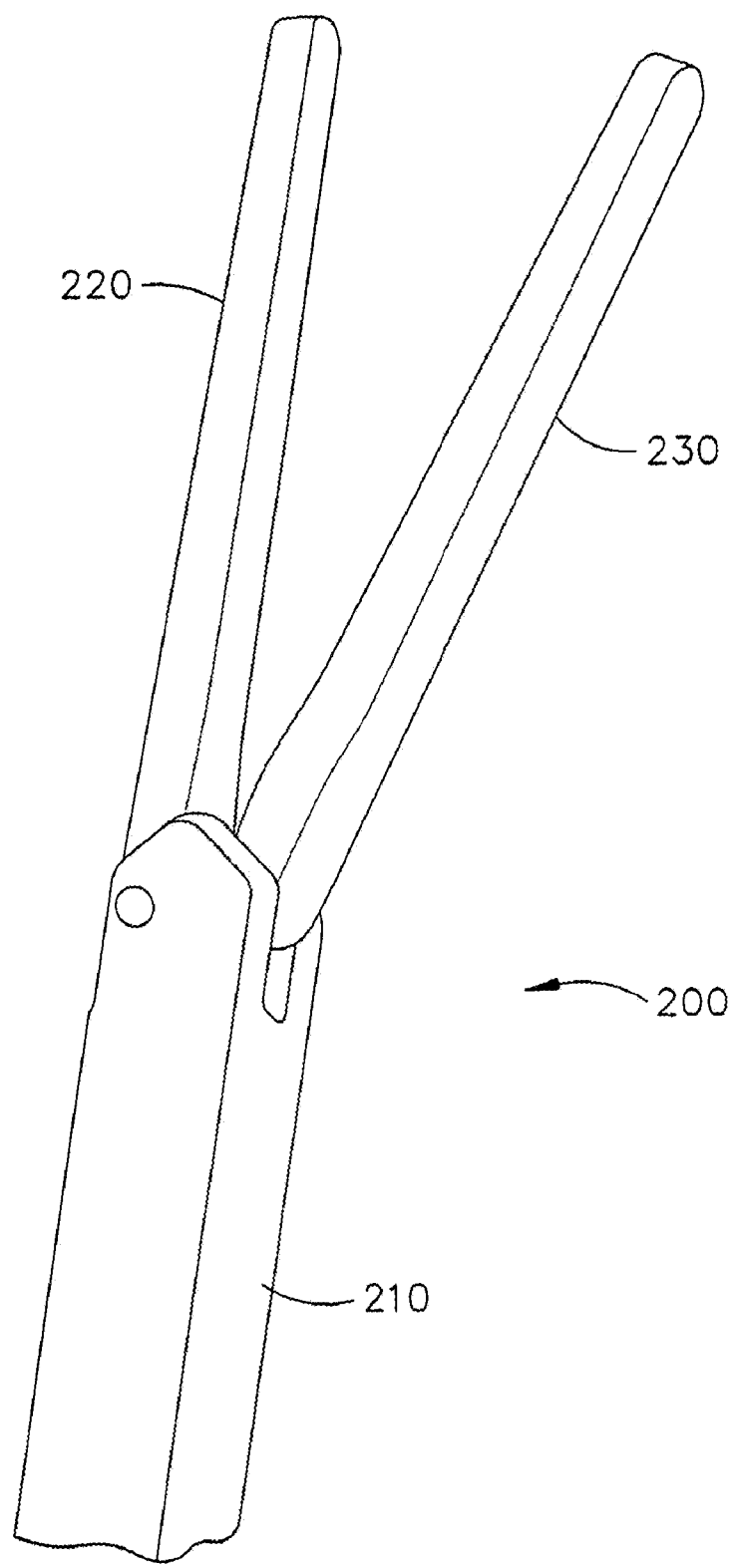
FIG. 3 illustrates an oblique view of an example of an articulated clamp in an opened position.

FIG. 3 illustrates another example of an articulated clamp 200. The clamp 200 includes a shaft 210, a distal jaw 220, and a proximal jaw 230. The shaft may be one or more of the following: straight, curved, rigid, flexible, malleable, and articulated. In this exemplary embodiment, the jaws are substantially straight; however, the jaws could also be curved in one or more directions. Similar to scissors-type motion, the jaws are pivotally moveable relative one another between an opened position and a closed position. As shown here, the jaws are in an opened position where the jaws are largely separated at a far end and not parallel to one another. In the closed position, the jaws are pivoted so they are adjacent and substantially parallel to one another. The distal jaw 220, proximal jaw 230, or both may pivot to effect the opening and closing.

Figure 4:
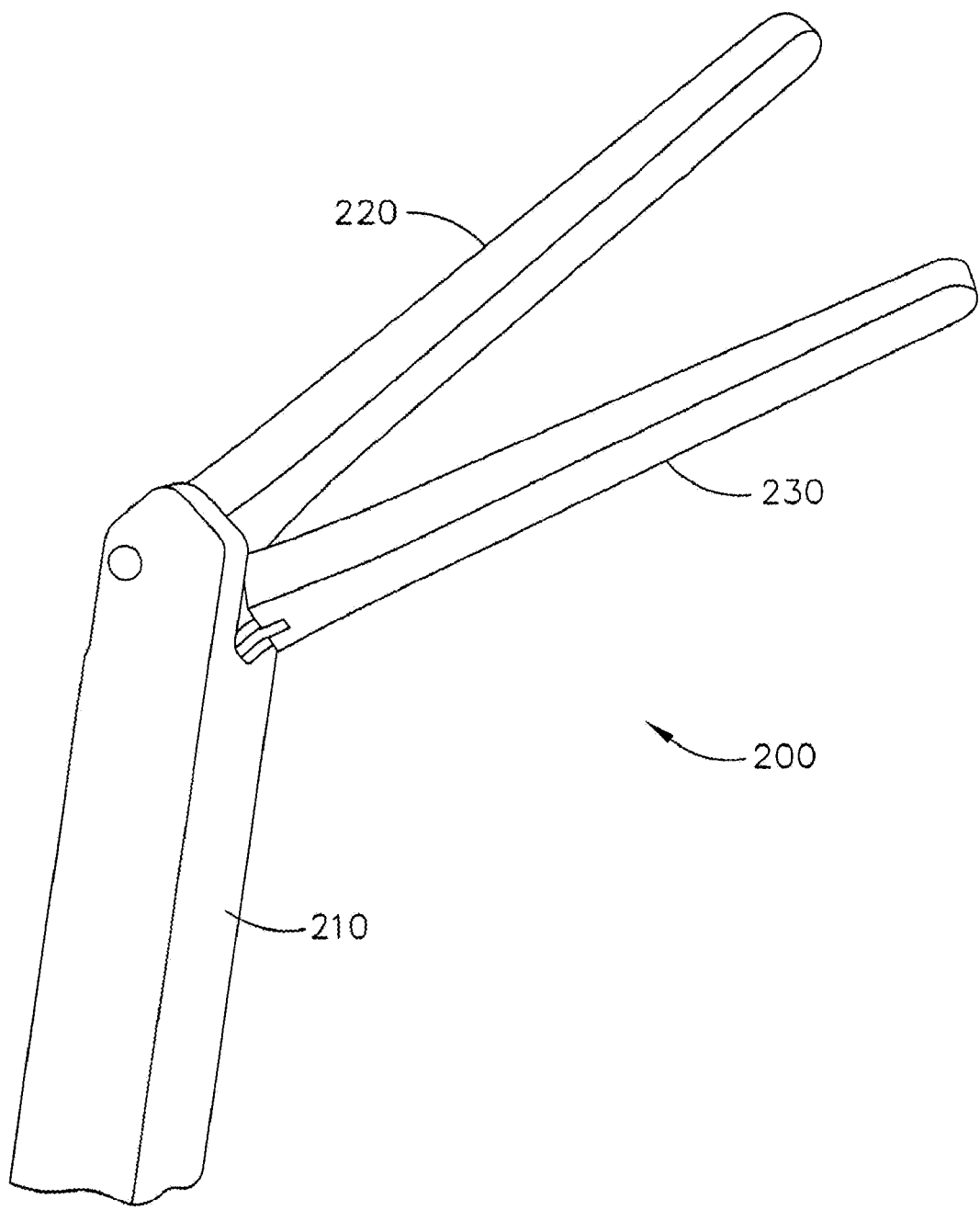
FIG. 4 illustrates an oblique view of the example articulated clamp of FIG. 3 in an opened position.

As shown in FIG. 4, the jaws 220, 230 have been articulated relative the shaft 210. In this exemplary embodiment, the jaws can be articulated relative the shaft 210 independent of the jaw pivotal motion. Thus, the jaws may remain in the opened position, but can be articulated. Likewise, the jaws could articulate while the jaws are partially or completely closed. The jaw articulation could extend through a broad range of angles. As shown here, the articulation angle for the distal jaws 220 is between 0 and 45 degrees relative to a longitudinal axis of the shaft 210; however the articulation range could be much wider. For example, the jaws 220, 230 could each articulate from −90 to +90 degrees relative the shaft 210. The same or different actuator mechanism (not shown) may effect the jaw pivoting and jaw articulation.

Figure 5:
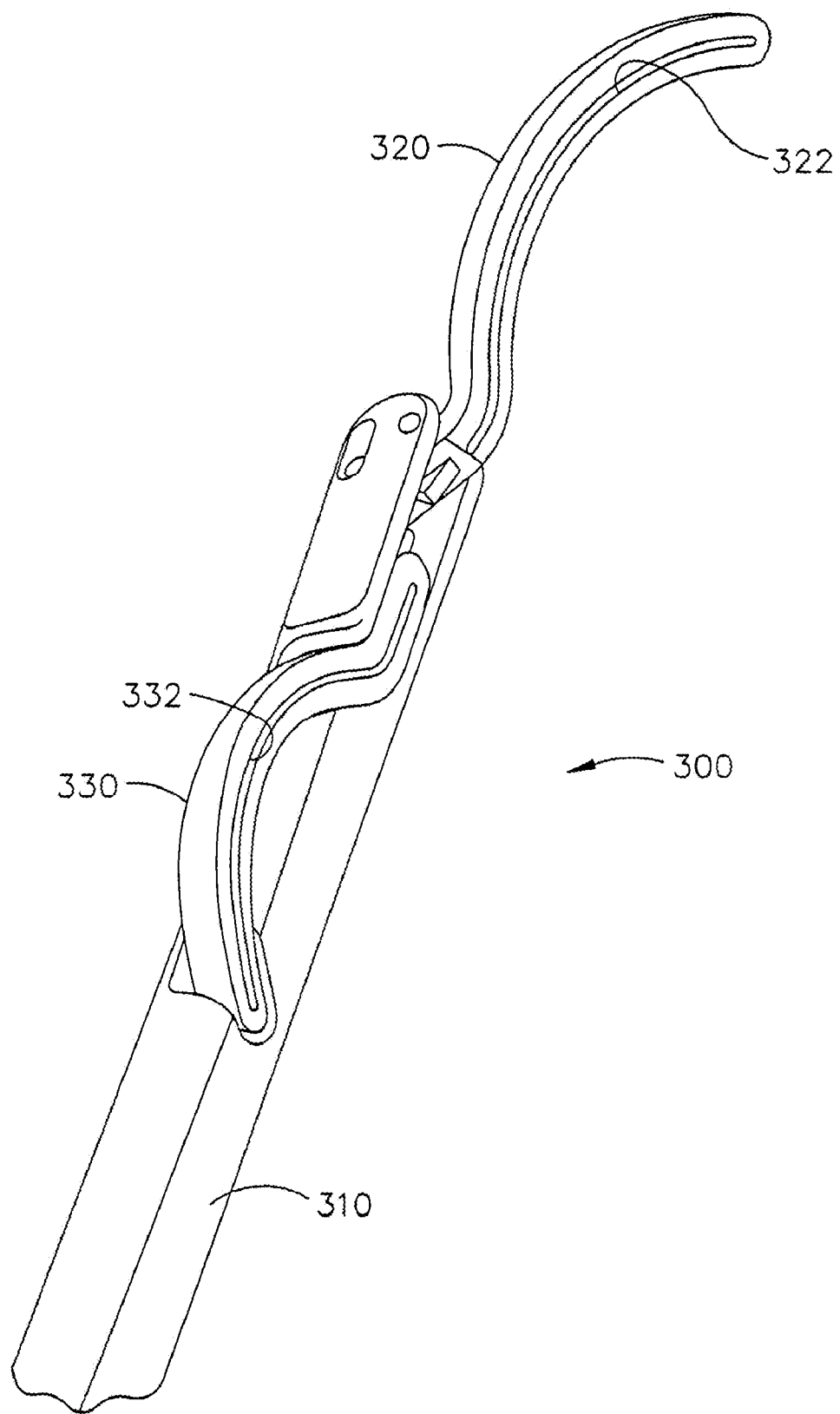
FIG. 5 illustrates an oblique view of an example of an articulated clamp in an articulated position.

FIG. 5 illustrates another example of an articulated clamp 300. The clamp 300 includes a shaft 310, a distal jaw 320, and a proximal jaw 330. The shaft may be one or more of the following: straight, curved, rigid, flexible, malleable, and articulated. In this embodiment, the jaws are curved; however, the jaws could also be straight or curved in other configurations. As shown here, the jaws are in an articulated position where the jaws are separated and not parallel to one another. As shown here, the distal jaw 320 extends distally relative to the shaft 310 and the proximal jaw 330 extends proximally relative to the shaft 310. In the present exemplary embodiment, the jaws each have an electrode 322, 332 to effect tissue ablation through bi-polar or mono-polar RF energy, for example.

Figure 6:
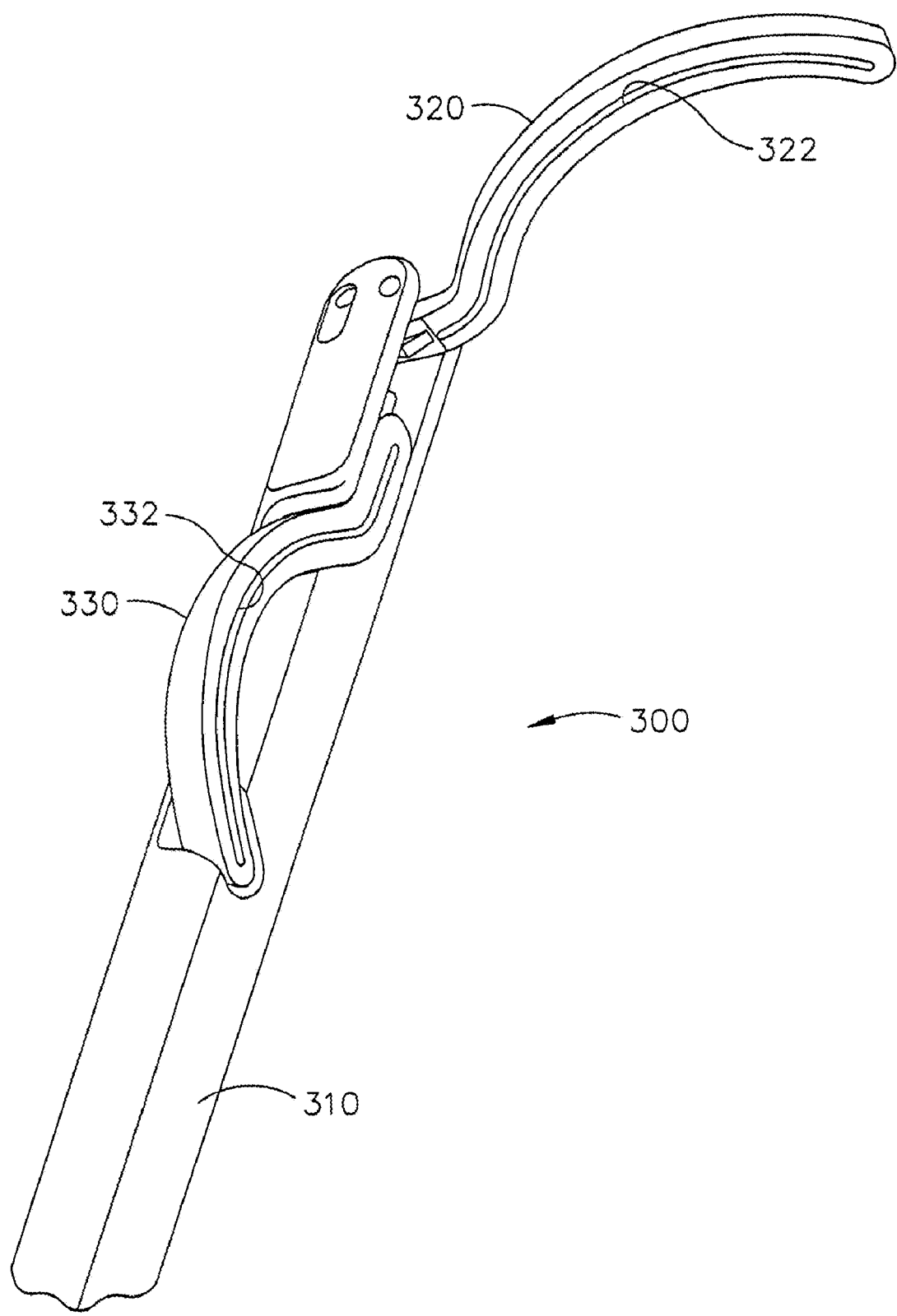
FIG. 6 illustrates an oblique view of the example articulated clamp of FIG. 5 in an articulated position.
Figure 7:
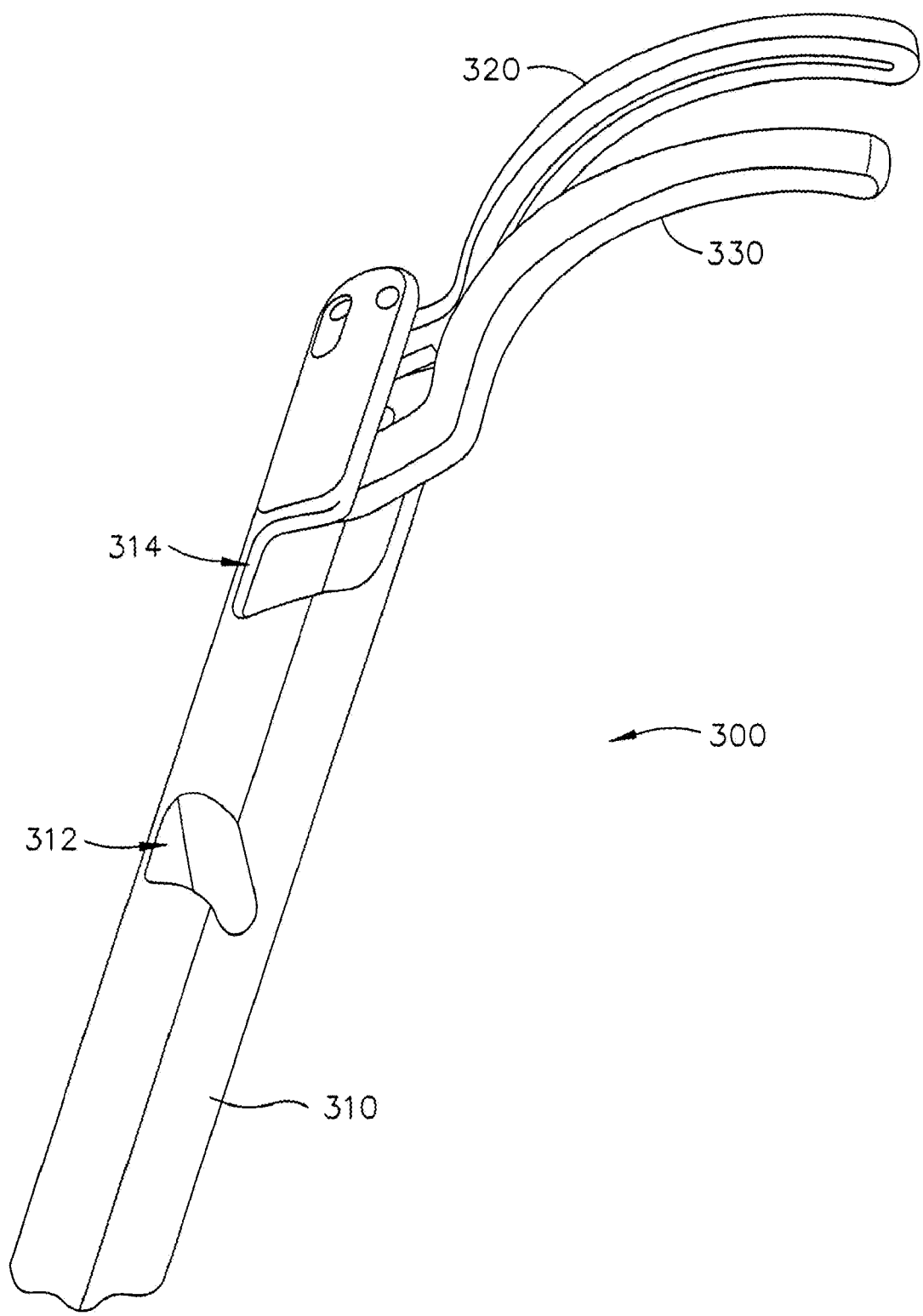
FIG. 7 illustrates an oblique view of the example articulated clamp of FIG. 5 in an opened position.

In this exemplary embodiment, the distal jaw 320 and/or proximal jaw 330 articulate relative to the shaft 310, either in cooperation with or independent of one another. For instance, FIG. 6 illustrates another articulated position where the jaws are separated and not parallel to one another. The distal jaw 320 has been articulated such that it extends laterally relative to the shaft 310, while the proximal jaw 330 has remained unmoved. FIG. 7 illustrates the articulate clamp 300 in an opened position where the jaws are separated and substantially parallel to one another. This view also illustrates recesses 312, 314 in the shaft 310 to receive the proximal jaw 330 when articulated in the fully proximal direction. The proximal jaw 330 has been articulated such that it extends laterally from the shaft 310. The jaws can then move to a closed position wherein the jaws are adjacent and substantially parallel to one another. As shown in this exemplary position, one or both of the jaws are axially repositionable relative to the shaft 310 such that the jaws remain parallel to one another between the opened and closed positions.

Note that the distal jaw 320 and/or proximal jaw 330 need not be axially aligned with the shaft 310 in the articulated positions. Likewise, the distal jaw 320 and proximal jaw 330 need not extend normal to the shaft 310 in the opened or closed positions. Instead, angular variations are contemplated, and in many cases may be advantageous based on the predicted anatomy or contemplated surgical procedure.

One advantage of articulated clamps (such as embodiments 100, 200, and 300) over an embodiment having relatively fixed orientation jaws is the ability to position the jaws of the articulated clamp more precisely proximate the target tissue. This ability is often desirable when operating on or near complicated or sensitive anatomical features and in minimally invasive surgical procedures. As a non-limiting example, the articulated clamp 300 may be used for open or minimally invasive surgery to treat atrial fibrillation by electrically isolating the left or right pair of pulmonary veins adjacent the left atrium. The articulated jaw positions facilitate positioning the device near the target tissue. The distal and/or proximal jaws may then be articulated to the opened position such that the tissue being treated is interposed between the jaws. The jaws may then be closed and the tissue ablated.

Figure 8:
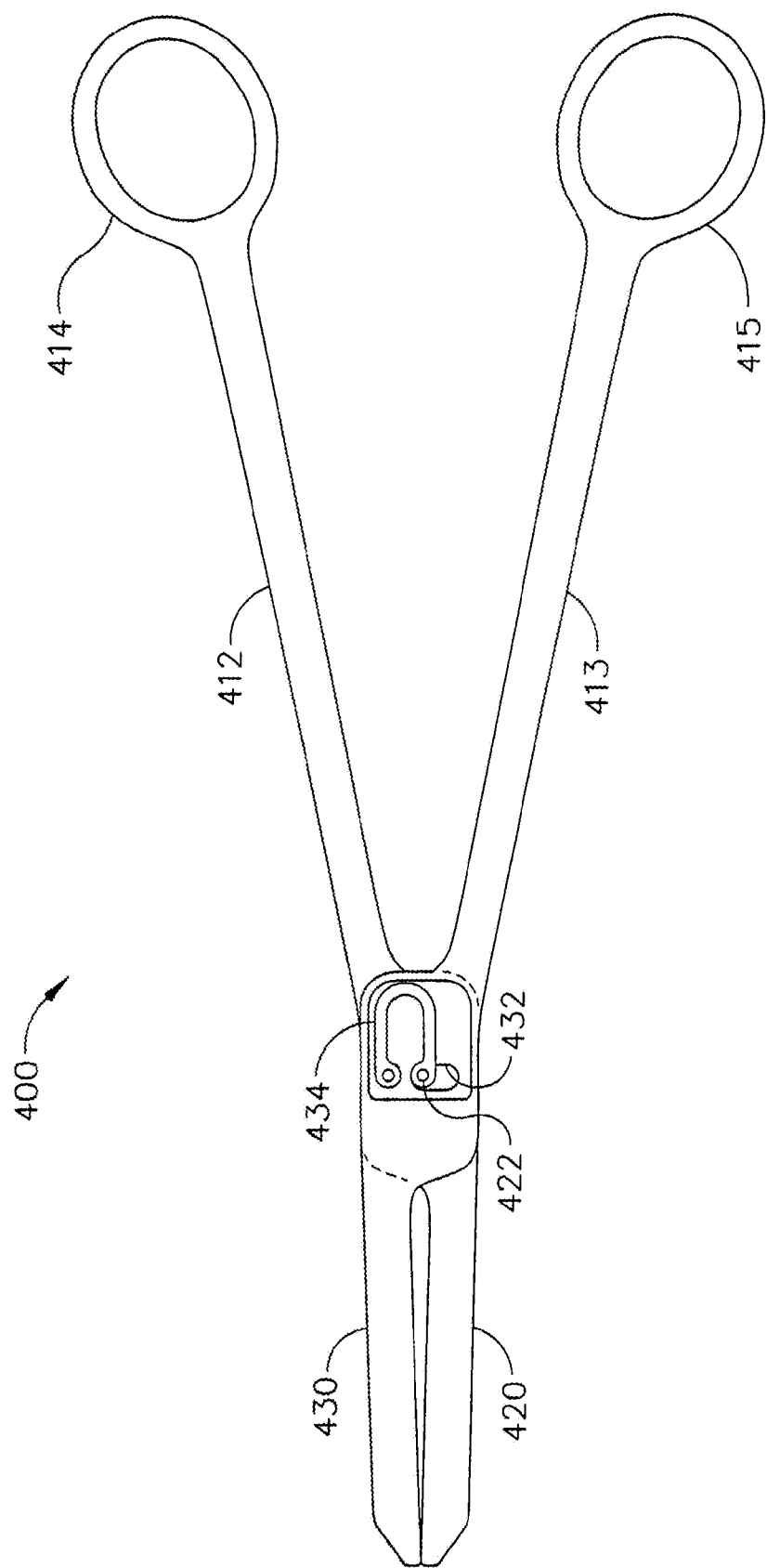
FIG. 8 illustrates a plan view of an example of a clamp with multiple degrees of freedom.

FIG. 8 illustrates an example of a scissor-type clamp 400 with multiple degrees of freedom. The clamp includes two clamp members 412, 413 in crossed relation to each other. Each clamp member has a distal end with a jaw 420, 430 and a proximal end with a handle 414, 415. In this embodiment, the jaws are substantially straight; however, the jaws could also be curved in one or more directions. Preferably, the clamping surfaces of the jaws 420, 430 have tissue ablation functionality, such as mono-polar or bi-polar electrodes. A joint 422 connects the two clamp members 412, 413 where they cross. The joint mates with a lateral slot 432. A biasing mechanism, which in this case is a U-shaped spring 434, biases the jaws 420, 430 towards one another along the lateral slot 432. Thus, this embodiment has two degrees of freedom. The first degree of freedom allows the relative rotation of the two clamp members 412, 413 about the joint. The second degree of freedom allows transverse movement between the two clamp members 412, 413.

One advantage of this embodiment 400 is the ability to clamp tissue while maintaining a substantially consistent clamping force along the lengths of the jaws. This is especially useful when clamping thicker tissue. The transverse degree of freedom prevents a disproportionate clamping force toward the pivot point of the joint 422. In addition, the spring 434 provides a maximum clamping force, which may be useful in certain procedures or to avoid traumatizing sensitive tissues.

Figure 9:
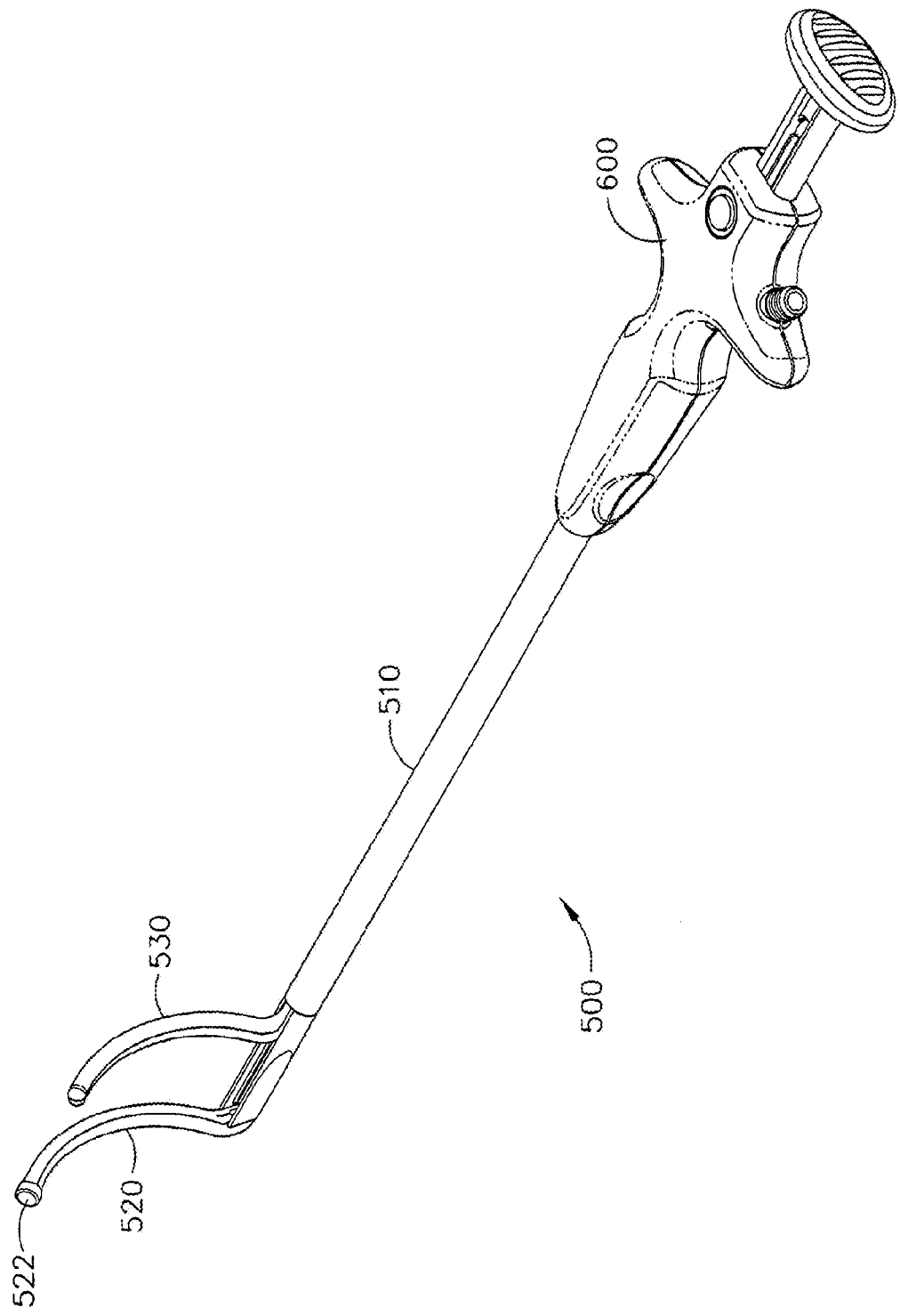
FIG. 9 illustrates an oblique view of an example of an articulated clamp.

FIG. 9 illustrates another example of an articulated clamp 500. This embodiment can be used to create lesions on the heart to treat atrial fibrillation. The clamp 500 includes a shaft 510, a distal jaw 520, a proximal jaw 530, and a handle 600. As shown here, the shaft 510 is straight and rigid; however, it could also be one or more of the following: curved, flexible, malleable, and articulated. In the present exemplary embodiment, the jaws 520, 530 each have slender electrodes (not shown) on the clamping surfaces to effect tissue ablation through bi-polar or mono-polar RF energy, for example. The jaws 520, 530 are curved; however, the jaws could also be straight or curved in other configurations. As shown here, the jaws 520, 530 are in an opened position where the jaws are separated and substantially parallel to one another. The jaws both extend laterally relative the shaft 510, but not necessarily normal the shaft. The proximal jaw 530 can be longitudinally repositioned relative to the shaft 510 independent of the distal jaw 520. In this example, the distal jaw 520 is fixed in position relative the shaft 510. Preferably, in this exemplary embodiment, the proximal jaw 530 locks in position parallel to the distal jaw 520 when the jaws are adjacent and in the closed position or while the proximal jaw 530 is being moved toward the closed position. Those skilled in the art will understand that the articulated clamp 500 is an exemplary embodiment and does not operate to limit the claims, nor any aspects of the other exemplary embodiments disclosed herein.

Alternatively, however, the distal jaw 520 could be repositionable to move longitudinally along the shaft 510 to a closed position where the jaws 520, 530 are adjacent and substantially parallel to one another. Preferably, in this alternate exemplary embodiment, the distal jaw 520 locks in position parallel to the proximal jaw 530 when the jaws are adjacent and in the closed position or while the distal jaw 520 is being moved toward the proximal jaw 530.

In one exemplary variation, the distal jaw 520 able to be articularted (e.g., pivoted) and is "limp" when articulating. Accordingly, in such a circumstance, the distal jaw 520 articulates passively in response to minimal external forces. Optionally, the tip of the distal jaw 520 includes a fastener 522, shown here as a female member, dimensioned to interface with a male fastener counterpart of an instrument guide (not shown). For instance, the instrument guide can be an elongate flexible member. When the instrument guide is anchored to the fastener 522, the distal jaw 520 may be positioned to a desired location in the surgical field by pulling the instrument guide. Preferably, the distal jaw 520 will be in its articulated "limp" position so as to reduce interference with surrounding or adjacent anatomical features. The distal and proximal jaws may then be adjusted so that the tissue being treated is interposed between the jaws 520, 530. The jaws may then be closed and the tissue ablated. After treatment is concluded, and the clamp is opened, the distal jaw 520 will return to its articulated "limp" position, thereby repositioning the instrument guide from the surgical area. Examples of instrument guides and exemplary surgical procedures are disclosed in U.S. patent application Ser. No. 11/254,057, filed on Oct. 19, 2005 and published as U.S. Patent Application Publication No. 2006/0167478, each of which is incorporated herein by reference.

Figure 10:
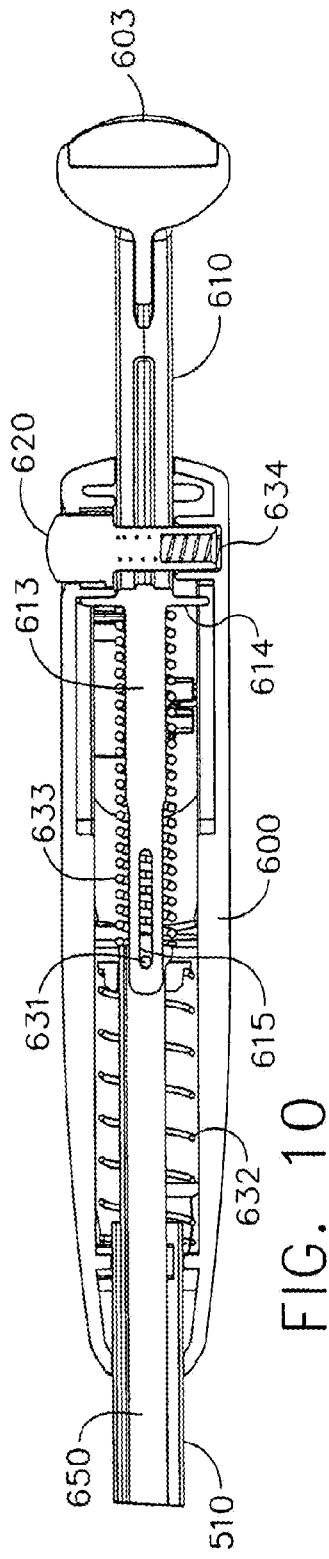
FIG. 10 illustrates a cross-sectional view of the actuator of the example articulated clamp of FIG. 9.
Figure 11:
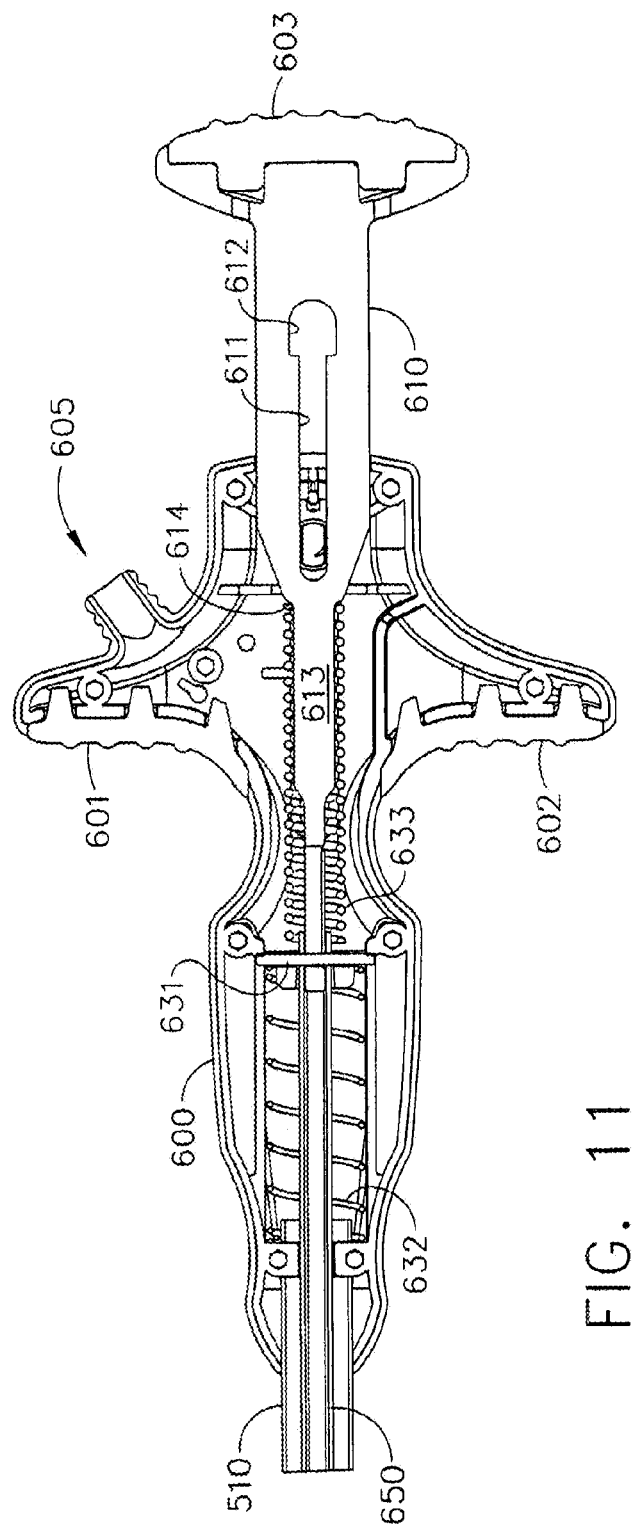
FIG. 11 illustrates a cross-sectional view of the actuator of the example articulated clamp of FIG. 9.

FIGS. 10 and 11 illustrate some features of the articulated clamp handle 600. The handle includes grips 601, 602, 603. A port 605 is provided through which wires or tubes may extend from the interior to the exterior of the handle. For instance, wires for the ablation electrodes or sensors on the jaws 520, 530 can be threaded through the shaft 510 into the handle 600 and out through the port 605.

The handle 600 also houses an actuator mechanism. In this example a plunger 610 is used to actuate the jaws 520, 530. Here, the plunger 610 is aligned with the shaft 510. In the fully retracted or proximal position (as shown), the distal jaw 520 is in its articulated "limp" position. When the plunger 610 is depressed in the distal direction, the distal jaw 520 locks into an open position parallel with the proximal jaw 530. Further depression will move the proximal jaw 530 distally towards the closed position. The plunger 610 includes a slot 611 with an opening 612. When the jaws are in the closed position, the opening 612 aligns with the lock 620. A spring 634 forces the lock 620 into the opening 612 preventing the plunger 610 from moving proximally, thus maintaining the jaws in the closed position. Depressing the lock 620 will release the plunger 610 thus allowing proximal movement.

An actuator rod 650 actuates the jaws. Distal movement closes the jaws while proximal movement opens the jaws. The plunger 610 includes a relief rod 613 surrounded in a force limiting spring 633. The force limiting spring 633 is compressed between the step 614 and the actuator rod 650. Depressing the plunger 610 imparts a load on the force limiting spring 633 that is translated to the actuator rod 650, which will move the actuator rod 650 distally. A return spring 632 is operative to move the actuator rod 650 proximally upon releasing the plunger 610. If the jaw clamping load exceeds load of the force limiting spring 633, the slot and pin 615, 631 interface allows the relief rod 613 to move distally without moving the actuator rod 650. Thus, the force limiting spring 633 effectively defines the maximum jaw clamping load. One with ordinary skill in the art will recognize that the tissue clamping pressure is a function of the jaw clamping load and the tissue area being clamped.

While not required, the jaws will preferably move between the opened and closed positions in a 1:1 ratio relative the motion of the plunger 610. Likewise, the jaw clamping load preferably will have a 1:1 ratio relative the depression load on the plunger 610. One advantage of the 1:1 relative ratios of movement and/or load is to improve tactile feedback from the jaws to the surgeon during a surgical procedure.

Figure 12:
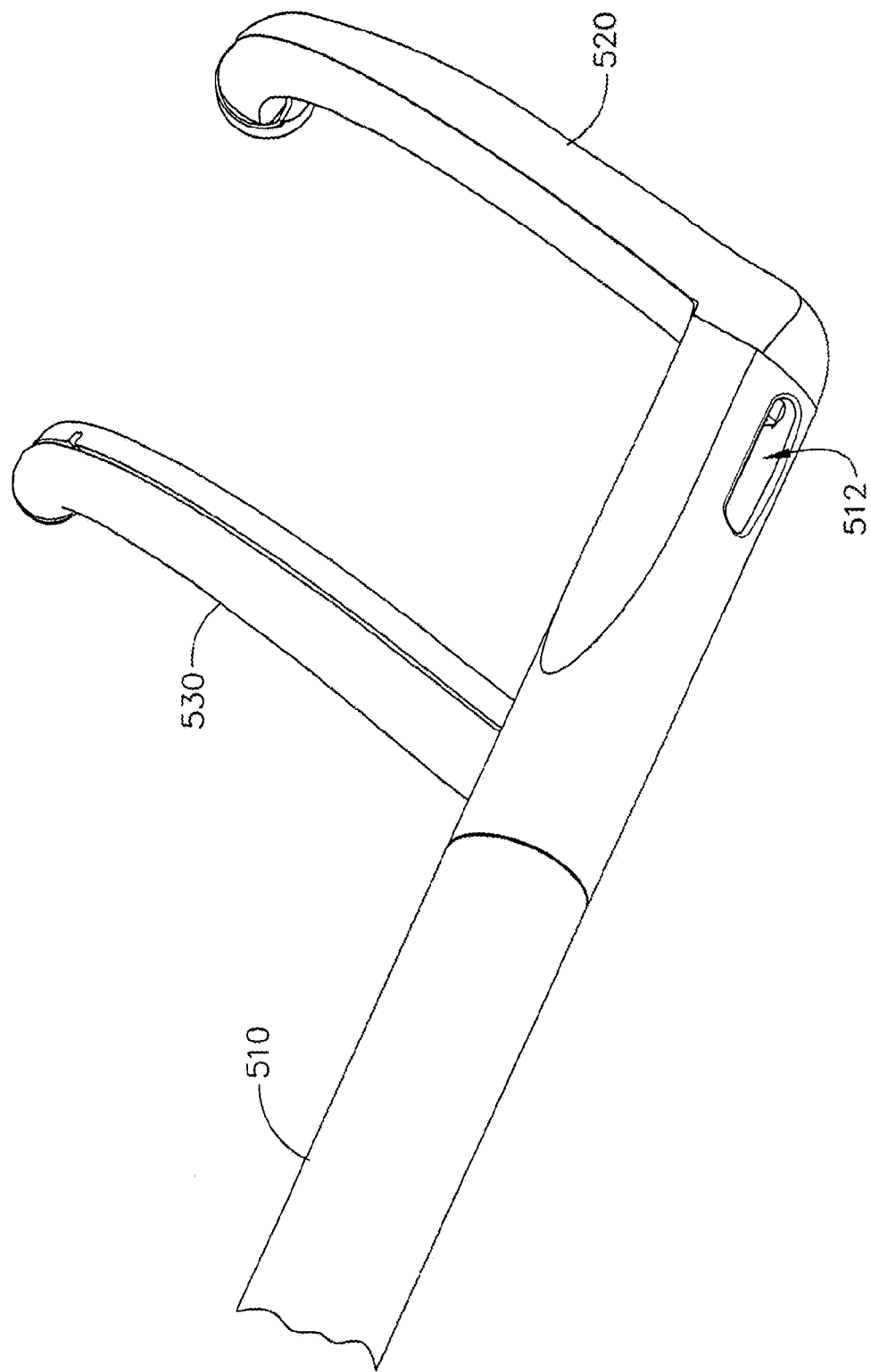
FIG. 12 illustrates an oblique view of the distal end of the example articulated clamp of FIG. 9.

FIG. 12 shows a rear view of the distal end of the clamp 500 in the opened position. The shaft 510 includes a weep hole 512 to help drain fluids.

FIGS. 13-16 illustrate an exemplary mechanism 700 to articulate, open, and close the jaws of a clamp, where both jaws are repositionable. These figures show a shaft 710, a distal jaw 720, and a proximal jaw 730. An actuator rod 750 is positioned in the shaft 710 and is attached to the proximal jaw 730. Axial movement of the actuator rod 750 is translated to axial movement of the proximal jaw 730. The proximal jaw 730 extends laterally relative the shaft 710 at a substantially constant angle. Connected to the proximal jaw 730 is a guide pin 732 seated in a longitudinal slot 712 in the shaft 710. The guide pin/slot interface prevents the proximal jaw 730 from rotating about the longitudinal axis of the shaft 710 regardless of the position of the proximal jaw 730 along the length of the longitudinal axis.

The distal jaw 720 pivots with respect to the shaft 710 about the pin 722. A locking rod 740 is pivotally connected to the distal jaw 720 via a pin 742. A follower pin 744 is connected to the locking rod 740 and is seated in an L-shaped locking slot 714 in the shaft 710 and a stepped follower slot 752 in the actuator rod 750.

Figure 13:
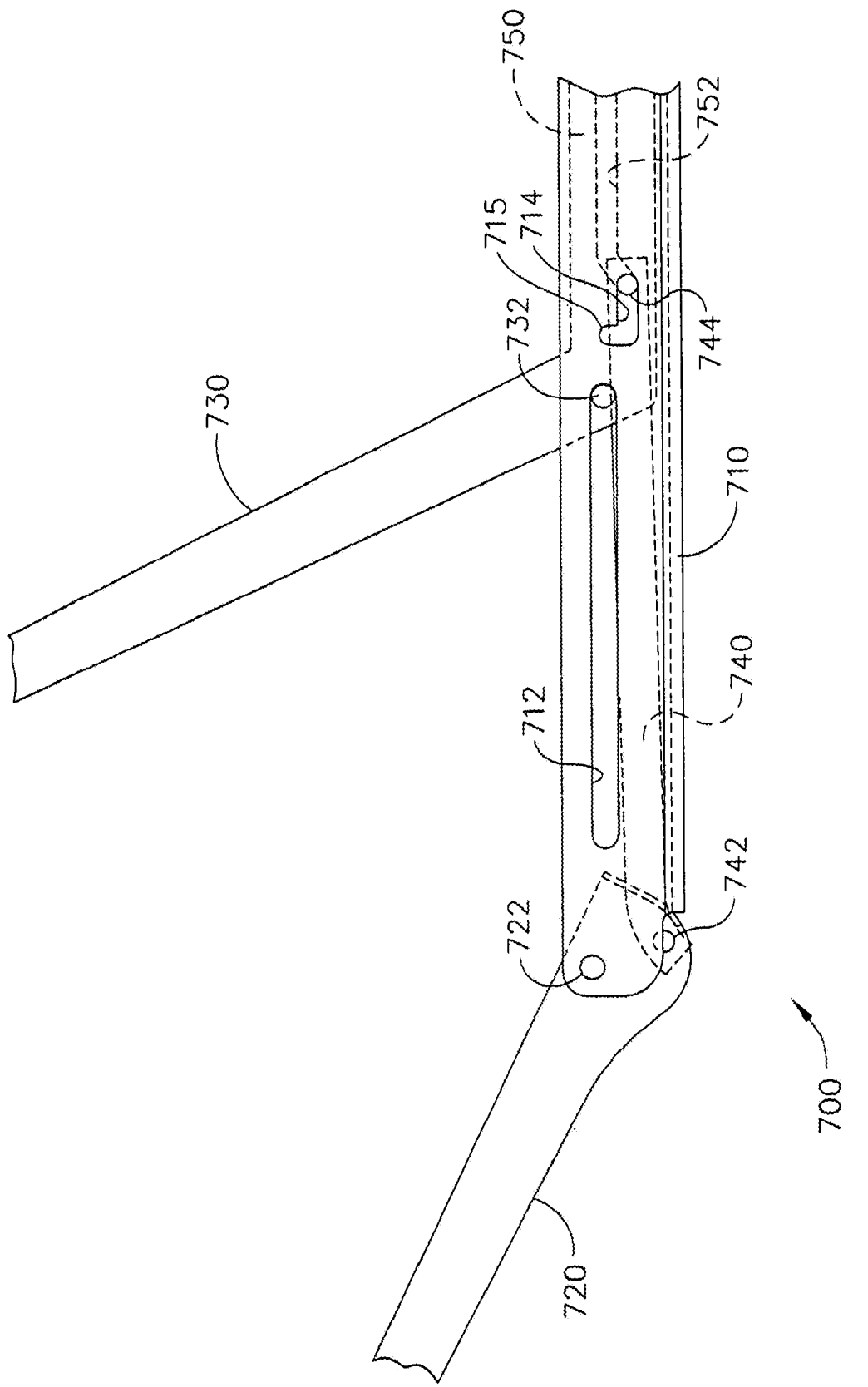
FIG. 13 illustrates a side view of an example of linkages to effect articulation of a clamp.
Figure 14:
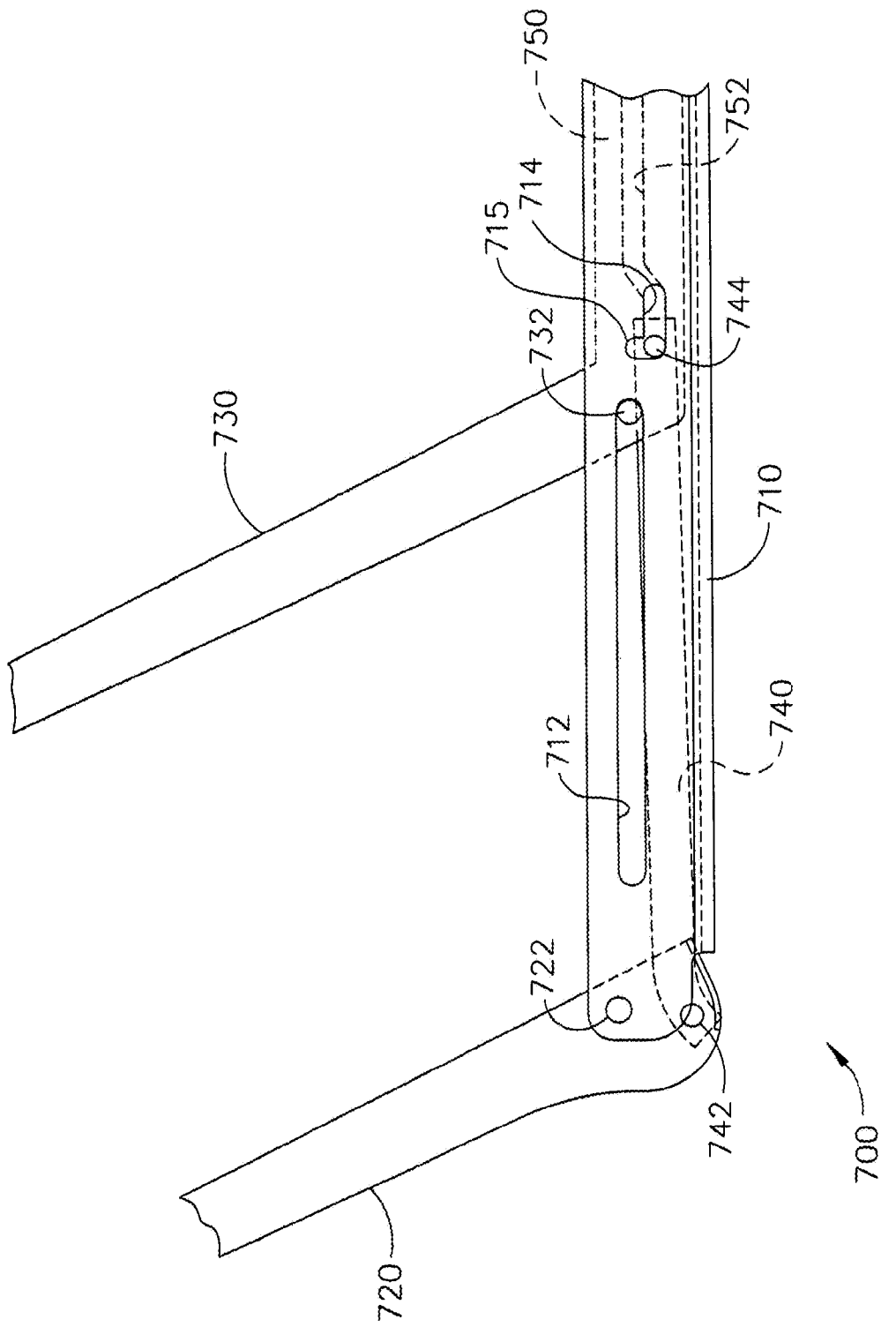
FIG. 14 illustrates a side view of an example of linkages to effect articulation of a clamp.

FIGS. 13 and 14 illustrate the passive articulation of the distal jaw 720 while the actuator rod 750 is in its proximal-most position. FIG. 13 shows the distal jaw 720 in its fully articulated position and FIG. 14 shows the distal jaw 720 in an open position where the jaws 720, 730 are separated and oriented substantially in parallel to one another. As the distal jaw 720 articulates/rotates about the pin 722, the follower pin 744 moves longitudinally within the limits of the axial portion of the locking slot 714.

Figure 15:
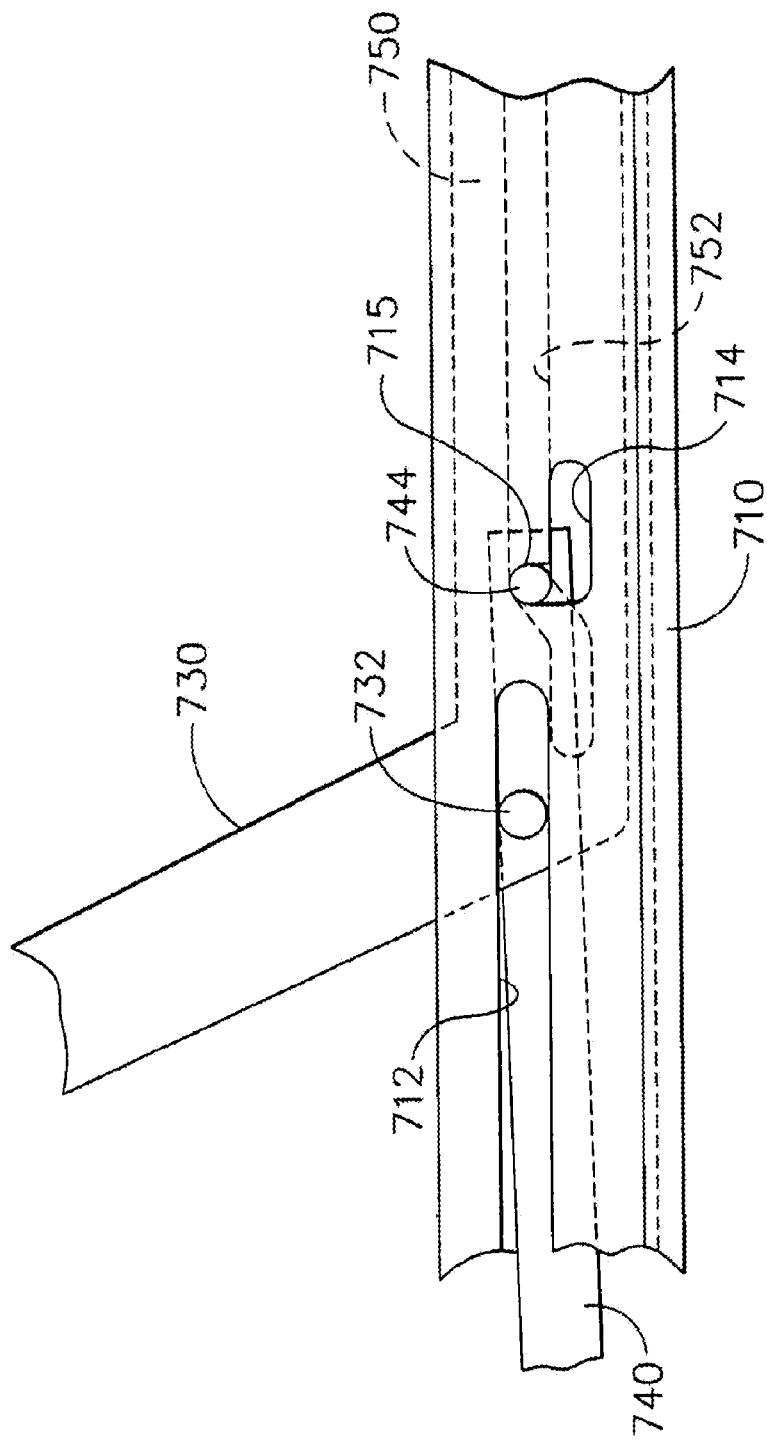
FIG. 15 illustrates a side view of an example of linkages to effect articulation of a clamp.

In FIG. 15, the actuator rod 750 has been repositioned distally. If the distal jaw 720 is in an articulated position, the step in the follower slot 752 operates to push the follower pin 744 distally, thus rotating the distal jaw 720 to the opened position (see FIG. 14). The angled step in the follower slot 752 also pushes the follow pin 744 upward in the locked portion 715 of the slot 714, as shown in FIG. 15. In this position, longitudinal movement of the follower pin 744 is restricted, thus locking the distal jaw 720 in a position substantially parallel to the proximal jaw 730.

Figure 16:
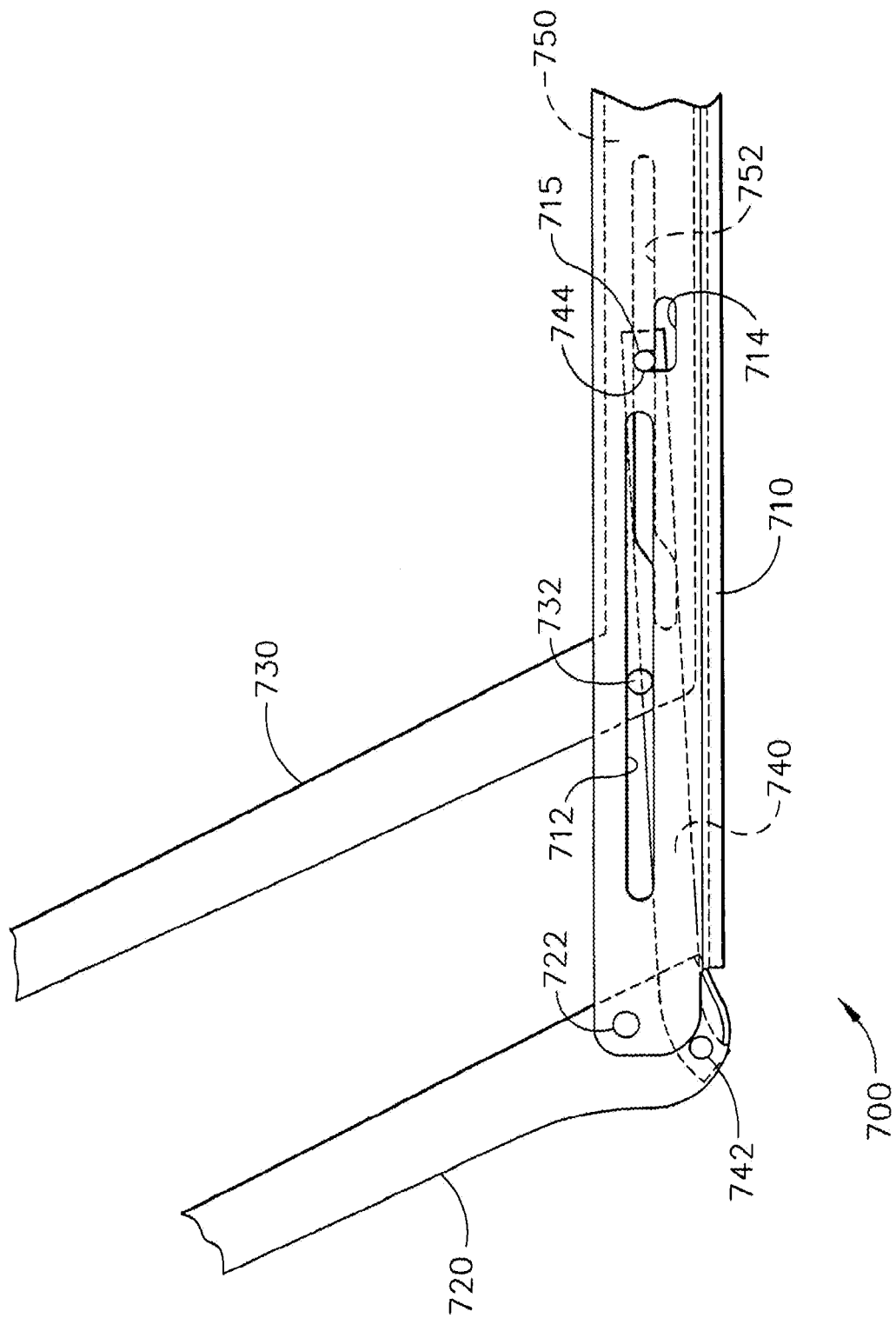
FIG. 16 illustrates a side view of an example of linkages to effect articulation of a clamp.

FIG. 16 illustrates the actuator rod 750 being moved further in the distal direction. The proximal jaw 730 advances towards the distal jaw 720 and a closed position. The follower pin 744 remains in the locked position within the locking portion 715. The follower pin 744 is also in the upper step of the follower slot 752 so longitudinal movement of the actuator rod 750 is unrestricted.

Figure 17:
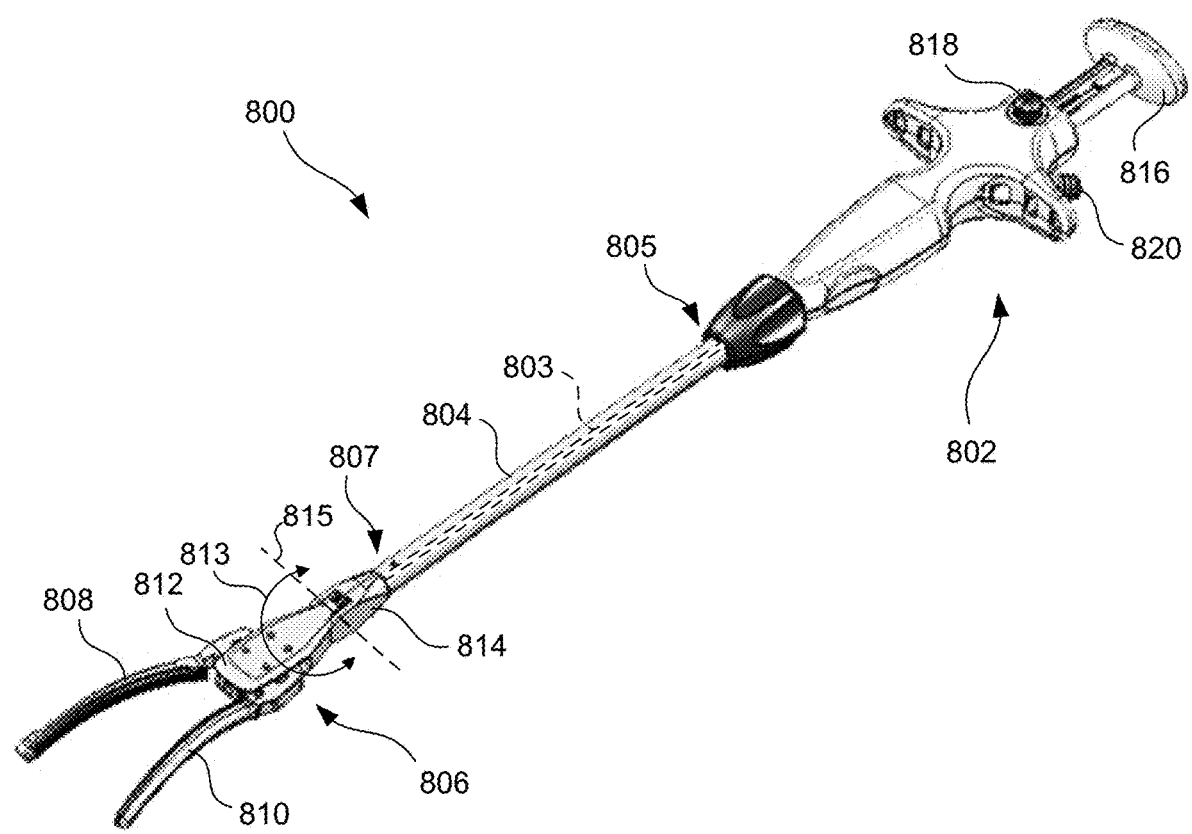
FIG. 17 is a perspective view of an exemplary clamp.

As illustrated in FIG. 17, another exemplary clamp 800 includes a handle 802, a shaft 804, and an end effector 806. An exemplary end effector 806 includes a first jaw 808 and a second jaw 810, which may be movable with respect to a head 812. Jaws 808, 810 extend generally distally from head 812 in a Y-shaped or V-shaped configuration. An exemplary head 812 is pivotable relative to the shaft 804 about an articulating joint 814. For example, head 812 is pivotable as illustrated by arc 817 about a transverse axis 815. An exemplary shaft 804 includes a proximal end 805 and a distal end 807, and some exemplary shafts 804 include rigid or substantially rigid portions and/or substantially flexible or deformable portions. An exemplary handle 812 includes at least one of: one or more plungers 816, one or more lock release buttons 818, and one or more ports 820. Plunger 816 is operatively connected to end effector 806 by one or more linkages, such as band 803 extending through shaft 804. Other example linkages include rods, cables, chains, and/or other suitable connectors known in the art. Some example embodiments include one or more linkages configured to transmit substantial forces in compression and tension (e.g., a rod with sufficient buckling strength). Some exemplary embodiments include one or more linkages configured to transmit substantial forces only in tension (e.g., a substantially flexible cable).

In some example embodiments, end effector 806 includes one or more rotating offsets (e.g., gears, pulleys, cranks, arms, rods, etc.) configured to articulate individual jaws 808, 810. For example, FIGS. 18-22 illustrate an exemplary end effector 806 including a double-gear actuating mechanism 813. As another example, FIGS. 25-28 illustrate an exemplary end effector 1806 including a cable-driven actuating mechanism 1813.

Figure 18:
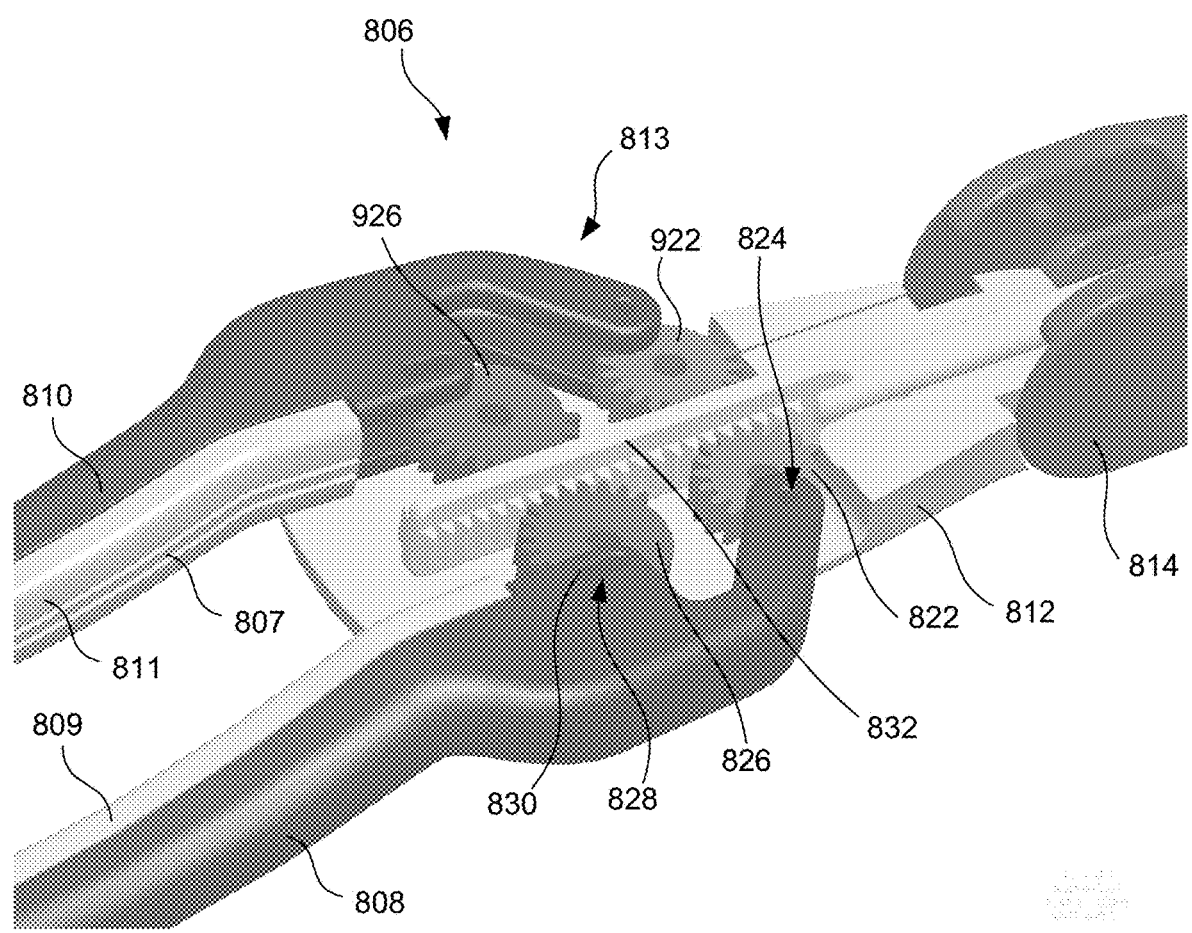
FIG. 18 is a detailed partial cutaway view of an exemplary double-gear end effector.

FIG. 18 is a partial cutaway view of an exemplary end effector 806 including an exemplary double-gear actuating mechanism 813. The first jaw 808 is connected to the head 812 by an actuating mechanism 813 which includes one or more gears pivotably and/or slidably coupled to the first jaw 808. For example, the first gear 822 (an example of a rotating offset) is rotatably mounted to the head 812 at a stationary hub 823 and is connected to the first jaw 808 by a pin 824. A second gear 826 (also an example of a rotating offset) is rotatably mounted to head 812 at a stationary hub 825 and is connected to first jaw 808 by a pin 828 which is slidable within a slot 830 in first jaw 808. A rack 832 engages the first gear 822 and/or the second gear 826.

As used herein, the term "gear" refers to a rotating part including teeth which meshes with another toothed part. The circumferences of various gears described herein may be partially or fully toothed and/or may or may not be substantially circular. As used herein, "rack" refers to a substantially linear toothed component, such as a toothed bar or rod.

As will be recognized by one of ordinary skill in the art, the particular motion of the first jaw 808 resulting from movement of the rack 832 is determined by selection of the diameters and/or arrangement of the first gear 822 and/or the second gear 826, as well as the arrangement and/or size of slot 830 and/or the positions of pins 824, 828 on gears 822, 826. In an exemplary embodiment, the second jaw 810 is connected to head 812 by a similar double-gear mechanism, which may include a third gear 922 and/or a fourth gear 926. In some exemplary embodiments, the rack 832 is double-sided, meaning that it includes two toothed surfaces, which may be on generally opposite sides. Exemplary jaws 808, 810 include insulators 809, 811, which may at least partially encase one or more electrodes 807 associated with one or both of the jaws 808, 810.

Figure 19:
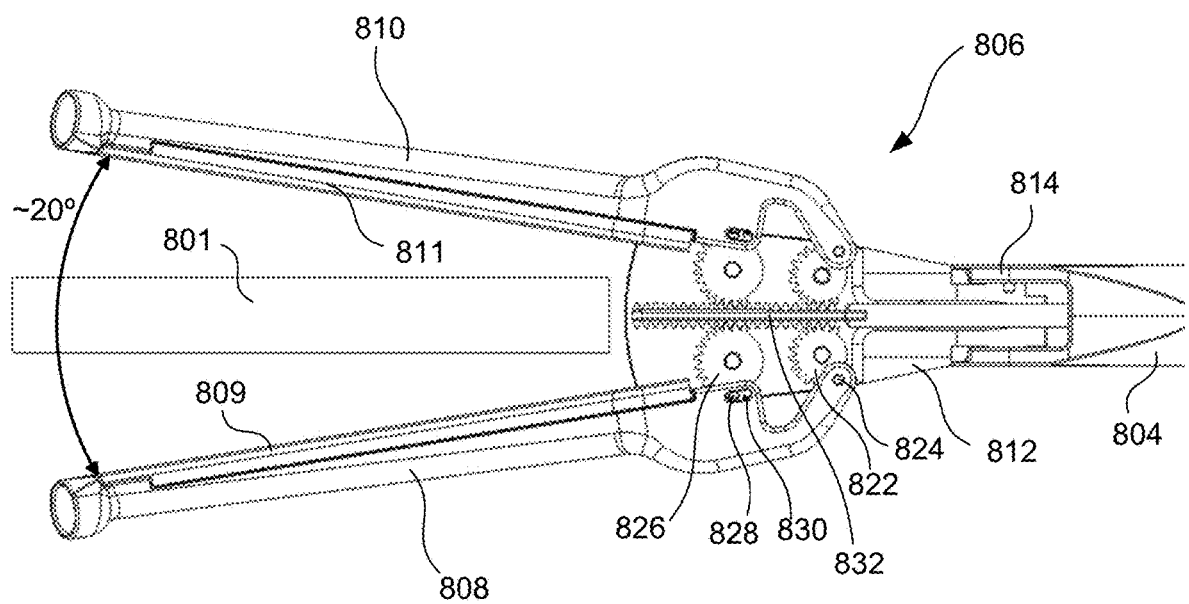
FIG. 19 is a detailed partial cutaway view of an exemplary double-gear end effector in an articulated position.

FIGS. 19-22 depict an exemplary end effector 806 operating from an open position to a closed position. FIG. 19 illustrates an exemplary open position in which the first jaw 808 and the second jaw 810 are separated and substantially non-parallel. Target tissue 801 may be positioned generally between the first jaw 808 and the second jaw 810. In the position shown in FIG. 19, the pin 828 is generally at or near the distal end 830A (also referred to as the leading end) of the slot 830, and the pins 824, 828 are generally laterally located with respect to the gears 822, 826.

Figure 20:
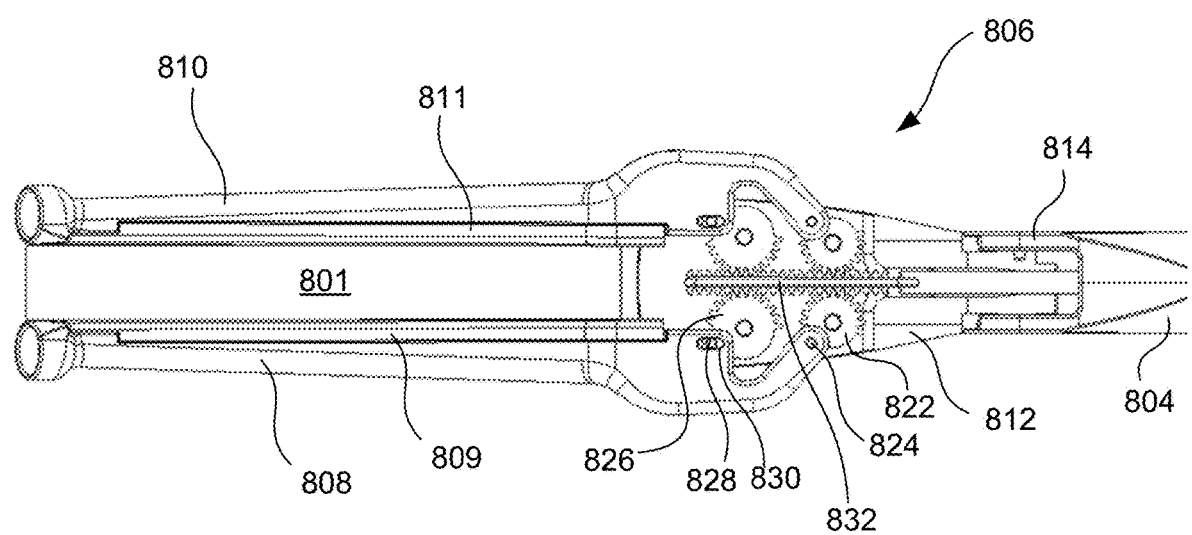
FIG. 20 is a detailed partial cutaway view of an exemplary double-gear end effector in an opened position.

FIG. 20 illustrates an exemplary contracted open position in which the first jaw 808 and the second jaw 810 are separated and substantially parallel. In this exemplary configuration, the first jaw 808 and the second jaw 810 are spaced apart about 8 mm in the open position. As is apparent from comparing the open position of FIG. 19 and the contracted open position of FIG. 20, the gears 822, 826 have rotated in a clockwise direction. This causes the first jaw to pivot relative to the gear 822 about the pin 824. Also, the first jaw pivots relative to the gear 826 about the pin 828, as well as translates relative to the gear 828 as the pin 828 moves partway along the length of the slot 830. Due to the difference in the diameters of the gears 822, 826 and the relative starting and ending positions of the pins 824, 828, this portion of the articulation operates to substantially change the angle of the jaw 808 from the open position of FIG. 19 to the contracted open position of FIG. 20.

Figure 21:
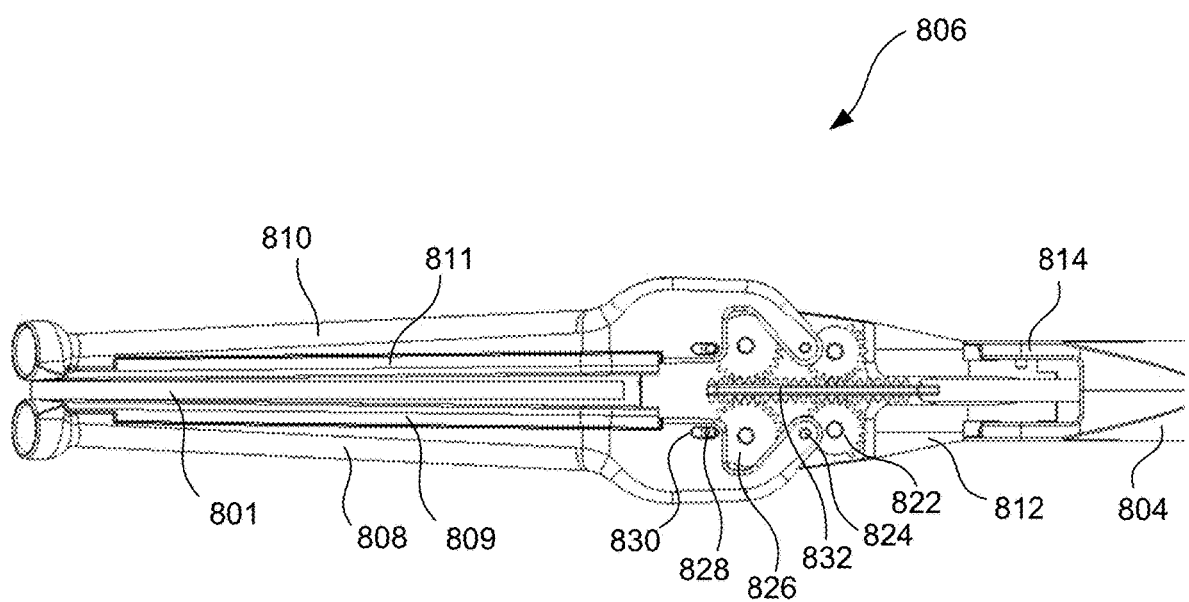
FIG. 21 is a detailed partial cutaway view of an exemplary double-gear end effector in an intermediate position.

FIG. 21 illustrates an exemplary intermediate position in which the first jaw 808 and the second jaw 810 are substantially parallel and have partially compressed the target tissue 801.

Figure 22:
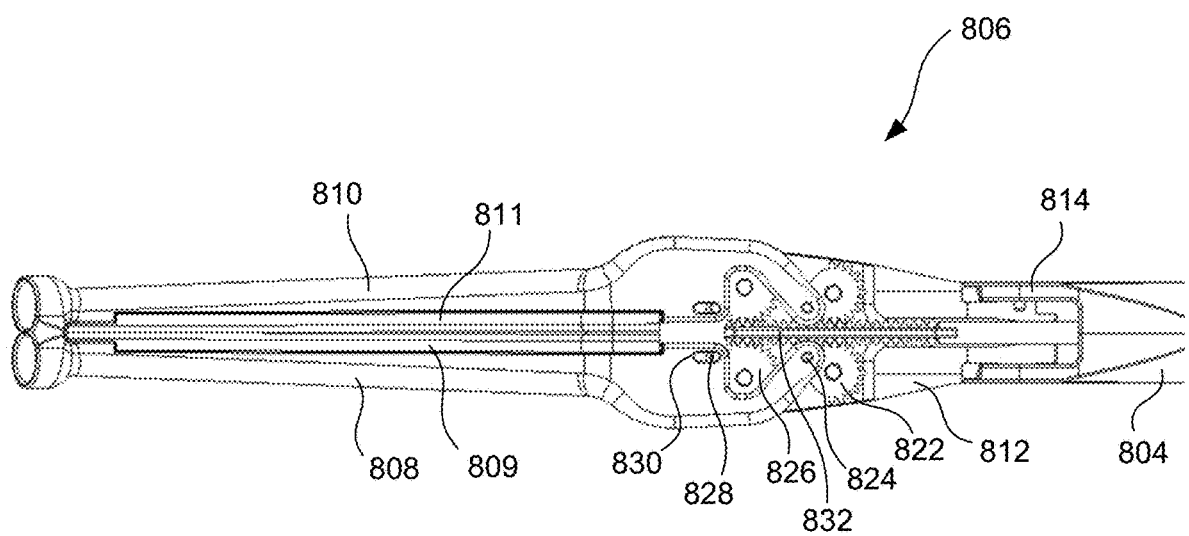
FIG. 22 is a detailed partial cutaway view of an exemplary double-gear end effector in an closed position.

FIG. 22 illustrates an exemplary closed position in which the first jaw 808 and the second jaw 810 are substantially adjacent and substantially parallel to one another. Comparing FIGS. 20-22 reveals that the pins 824, 828 have rotated past the distal ends of the gears 822, 826 as the jaw 808 moves from the contracted open position of FIG. 20, through the intermediate position of FIG. 21, and to the closed position of FIG. 22. This portion of the articulation generally causes the jaw 808 to close in a parallel fashion with little change in angular orientation because the pins 824, 828 move, substantially in parallel, in a generally medial direction. As the jaw 808 moves from the contracted open position of FIG. 20 to the closed position of FIG. 22, it continues to pivot relative to gear 822 about pin 824, and it continues to pivot relative to gear 826 about pin 828 while pin 828 translates towards the proximal end 830B (also referred to as the trailing end) of slot 830. Although the jaw 808 and the gears 822, 826 pivot relative to each other about the pins 824, 828, the orientation of the jaw 808 with respect to the head 812 remains substantially the same (e.g., approximately parallel with jaw 810) throughout this portion of the repositioning due to the arrangement of the pins 824, 828 on the gears 822, 826.

In this exemplary embodiment, the movement of the first jaw 808 and the second jaw 810 in FIGS. 19-22 is effected by movement of the rack 832 towards the shaft 804, which causes rotation of the first gear 822 and the second gear 826. In an alternate exemplary embodiment, the rack 832 is operatively coupled to the handle 812 by a linkage, such as a band 803 extending through the shaft 804. In the exemplary embodiment depicted in FIGS. 19-22, the band 803 is pulled (in tension) to move rack 832 towards the shaft, thereby closing the jaws 808, 810. In an alternate exemplary embodiment, a band 803 (or other linkage) may be extended (in compression) to actuate an end effector. For example, it will be apparent to one of skill in the art that a similar double-gear mechanism may be configured to close the jaws 808, 810 as the rack 832 moves away from the shaft 804. In such an embodiment, the band 803 (or other linkage) may be designed to have a relatively high buckling strength.

In this exemplary embodiment, the first gear 822 has a diameter of about 0.25 inches and the second gear 826 has a diameter of about 0.30 inches. In this exemplary embodiment, the first jaw 808 is angled with respect to the second jaw 810 at about 10-30 degrees (e.g., about 20 degrees) in the articulated position. This exemplary in-line clamp 800 is operable such that the first jaw 808 and the second jaw 810 open to about 35 mm and the articulating joint 814 allows about +/−30 degrees of movement of the end effector 806 relative to the shaft 804.

With reference to FIGS. 19-22, operation of the gears 822, 826 to manipulate the jaws from an open orientation as shown in FIG. 19, to a substantially parallel open position as shown in FIG. 20, and to a closed position as shown in FIG. 22 will be described. For purposes of this discussion, the operation of the gears and jaws will be described with reference to the centerline C of the end effector 806 where the centerline C is positioned at 12 o'clock with respect to each gear 822, 826. In the present embodiment, the rack 832 reciprocates along the centerline C, such that each gear 822, 826 mates with the rack 832 at the 12 o'clock point of each gear. The trailing end gear 822 has a slightly smaller diameter than the leading end gear 826, where both gears 822, 826 rotate about respective hubs 823, 825 that are spaced from the centerline C at a distance of their respective radiuses. The trailing end gear 822 is pivotally coupled to the trailing end of the jaw 810 at the pin 824 while the larger diameter, leading end gear 826 is coupled to the jaw 810 distal from the trailing end by a pin 828 seated in a slot 830 in the jaw 810, for a pivoting/sliding connection.

As shown in FIG. 19, in the articulated position, the trailing end gear pin 824 is at approximately the 5 o'clock position with respect to the centerline C, while the leading end gear pin 828 is at approximately the 6 o'clock position with respect to the centerline C, and the pin 828 is at the far leading end of the slot 830.

As shown in FIG. 20, in moving from the open position to the contracted open position, both gears 822, 826 are rotated such that the trailing end gear pin 824 is at approximately the 7 o'clock position and the leading end gear pin 828 is at approximately the 8 o'clock position and the pin 828 has slid back in the slot 830 toward the trailing end about mid-way. By virtue of the leading end gear pin 828 traveling a longer rotational distance than the trailing end gear pin 824, the leading end of the jaw 810 pivots towards the centerline C.

As shown in FIG. 21, further rotation of the gears 822, 826 moves their respective pins 824, 828 to approximately the 9 o'clock position, while the leading end gear pin 828 has slid further back towards the trailing end of the slot 830. As this rotation moves each pin substantially vertically toward the centerline C nearly the same vertical distance, and because the leading end gear pin 828 is sliding back within the slot 830 during this translation, the jaw 808 tends to move towards the centerline in an orientation that is substantially parallel with respect to the centerline C.

As shown in FIG. 22, in the closed position, the jaws 808, 810 are substantially parallel and substantially adjacent. Further rotation of the gears 822, 826 has moved their respective pins 824, 828 to approximately the 10 o'clock position, while the leading end gear pin 828 has slid further towards the trailing end of the slot 830. This rotation continues to move each pin substantially vertically toward the centerline C nearly the same vertical distance, and because the leading end gear pin 828 is sliding back within the slot 830 during this translation, the jaw 808 tends to move towards the centerline in an orientation that is substantially parallel with respect to the centerline C.

Figure 23:
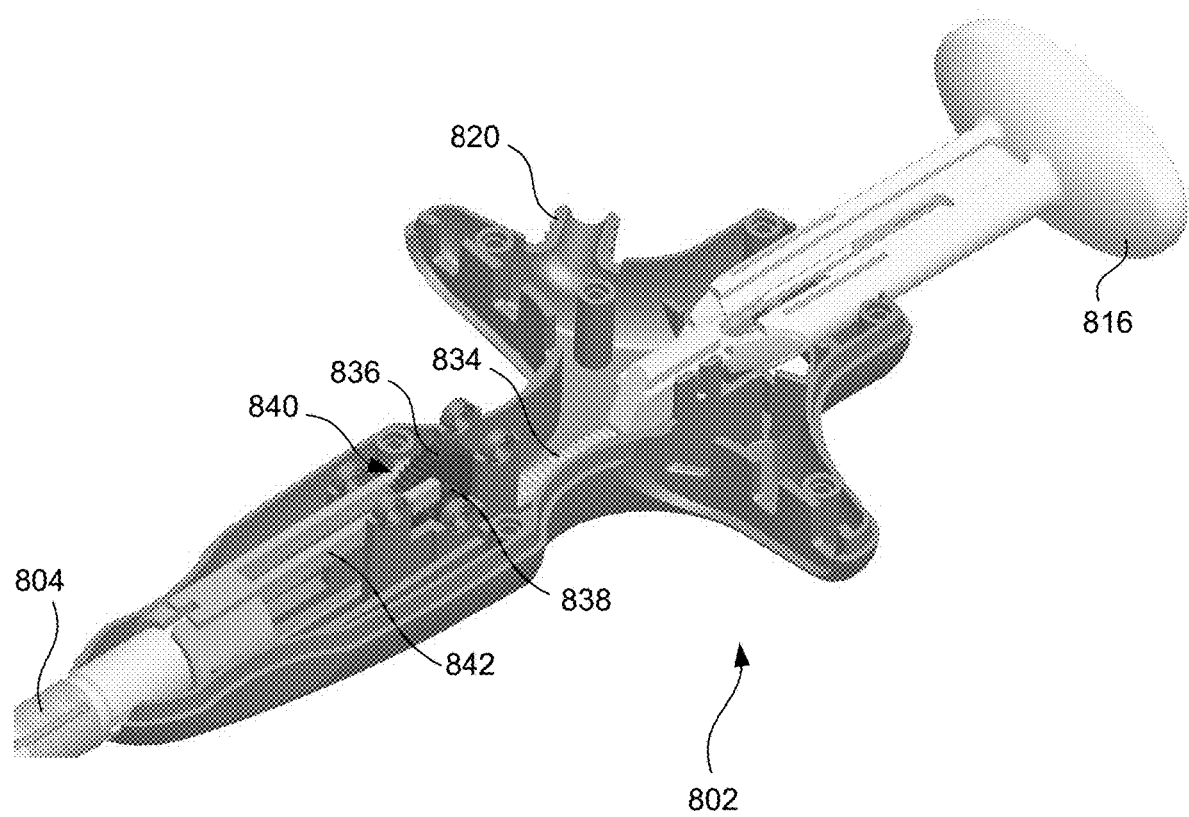
FIG. 23 is a detailed partial cutaway view of an exemplary handle.
Figure 24:
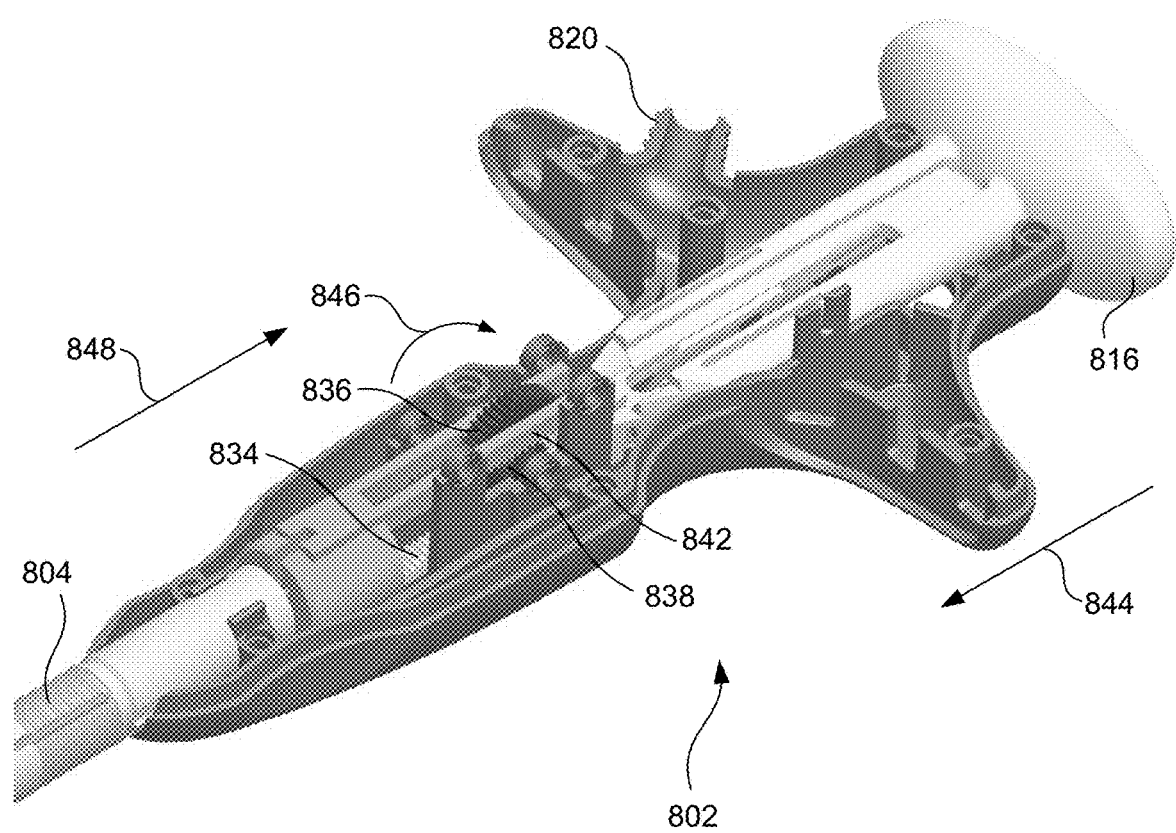
FIG. 24 is a detailed partial cutaway view of an exemplary handle.

FIGS. 23 and 24 are partial cutaway views of an exemplary handle 802. A plunger 816 includes a plunger rack 834, which is engaged with a spur gear 836 in a rack and pinion arrangement such that linear motion of the plunger rack 834 causes rotation of the gear 836 when the plunger 816 is depressed and/or extended. A spur gear 838 is affixed to the other spur gear 836, forming a compound gear 840. Rotation of the spur gear 838 causes linear motion of a linkage rack 842. For example, when the plunger 816 is depressed (e.g., moved in the direction of arrow 844), the plunger rack 834 causes the spur gear 836 to rotate in the direction of arrow 846, which results in rotation of the other spur gear 838 in the direction of the arrow 846. Rotation of the other spur gear 838 in the direction of the arrow 846 causes the linkage rack 842 to move in the direction of the arrow 848. Notably, the arrows 844 and 848 point in substantially opposite directions, indicating that the racks 834, 842 and the gears 836, 838 operate as a reversing mechanism. In some alternate exemplary embodiments, a linkage rack 842 may be coupled to a linkage (such as a band 803, see FIG. 17) operatively coupled to the rack 832 of the end effector 806. In such embodiments, depressing the plunger 816 causes the jaws 808, 810 to close.

Operation of the exemplary clamp 800 will now be discussed. With the jaws 808, 810 in the open position, the clamp 800 is placed so that the target tissue 801 lies between the jaws 808, 810. The plunger 816 is depressed, operating the reversing mechanism and exerting a pulling force on the linkage 803 (see FIG. 17). The linkage 803 pulls the rack 832 toward the handle 812 with respect to the end effector 806, thus causing rotation of the first gear 822 and the second gear 826. Rotation of the first gear 822 and the second gear 826 causes the jaws 808, 810 to rotate from the non-parallel open position to the substantially parallel open position (see FIG. 20). Once the jaws 808, 810 reach the substantially parallel open position, further depression of the plunger 816 causes the jaws 808, 810 to translate towards each other (towards the closed position) while remaining substantially parallel. Once the jaws 808, 810 have been closed to the desired extent, the lock is engaged. Ablation electrodes 807 located on one or both of the jaws 808, 810 are activated. When it is desired to remove the clamp 800, the lock is disengaged, and the plunger 816 is released. The jaws 808, 810 return to the open position and may be withdrawn from the target tissue 801.

Figure 25:
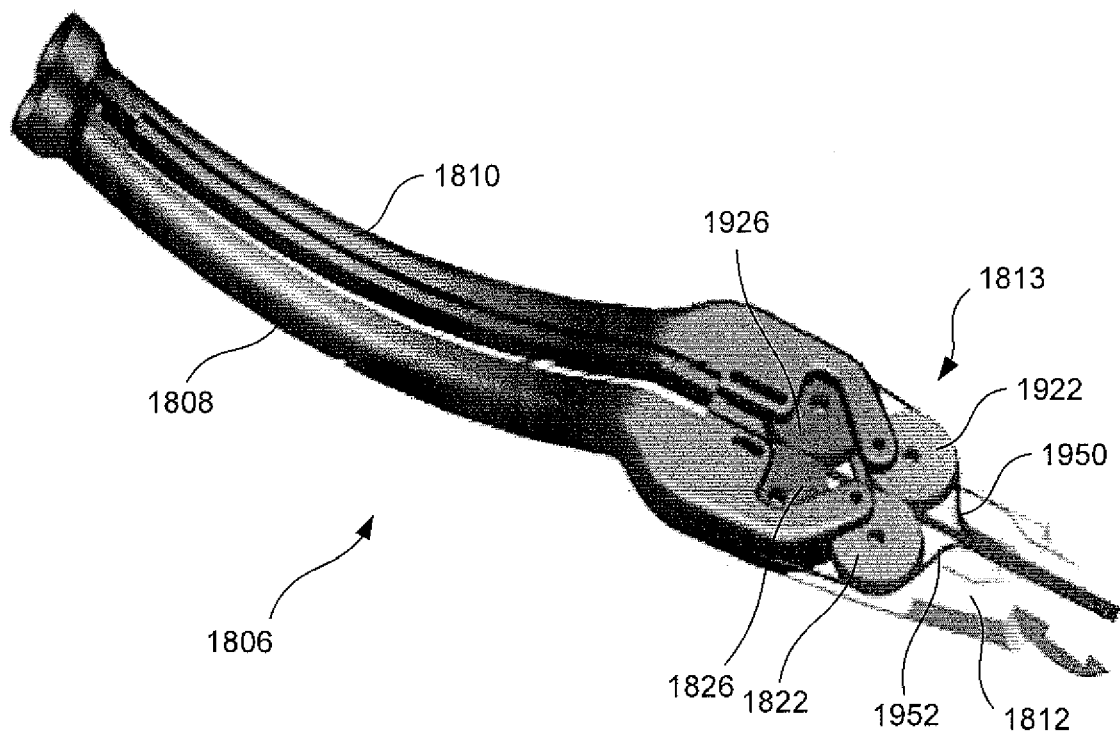
FIG. 25 is a partial cutaway view of an exemplary cable-driven end effector.

FIG. 25 illustrates an exemplary end effector 1806 including a cable-driven actuating mechanism 1813, which include one or more pulleys 1822, 1826, 1922, 1926. The pulleys 1822, 1826, 1922, 1926 are rotatably mounted to the head 1812. One or more cables 1950, 1952 engage one or more of the pulleys 1822, 1826, 1922, 1926. The cables 1950, 1952 and/or the pulleys 1822, 1826, 1922, 1926 cooperate to articulate the jaws 1808, 1810 in a manner generally similar to the double-gear embodiment described above. Individual cables 1950, 1952 comprise one or more segments and/or include a rope and/or other generally flexible materials that are tensioned to cause rotation of the pulleys 1822, 1826, 1922, 1926. For purposes of the present disclosure, a rope includes, without limitation, polymer lines and strands, metal lines and strands (e.g., a wire rope), polymer belts and metal belts, synthetic and natural rubber lines and strands, synthetic and natural rubber belts, aramid fiber, high-density polyethylene (HDPE), stainless steel (coated or non-coated), carbon fiber, boron fiber, and/or ultra high molecular weight polyethylene (UHMWPE) (e.g., SPECTRA).

Figure 26:
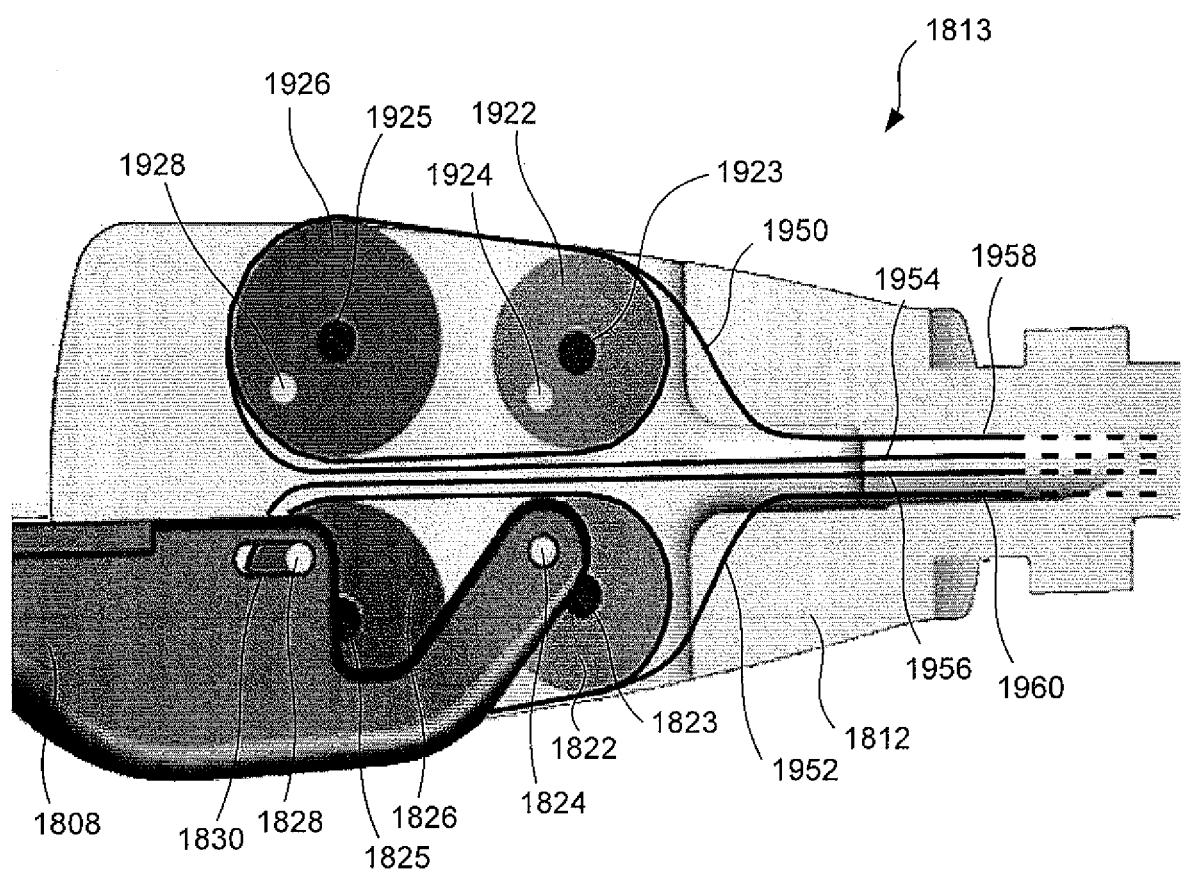
FIG. 26 is a detailed partial cutaway view of an exemplary cable-driven end effector.

FIG. 26 is a partial cutaway view of an exemplary cable-driven actuating mechanism 1813. Similar to double-gear mechanism 813 described above, the jaw 1808 is pivotably connected to the pulley 1822 by a pin 1824 and/or the jaw 1808 is pivotably and/or slidably connected to the pulley 1826 by a pin 1828, which is slidable within a slot 1830. The jaw 1810 is coupled to the pins 1924, 1928, which are mounted to the pulleys 1922, 1926 in a similar fashion. The pulleys 1822, 1826, 1922, 1926 are rotatably mounted to the head 1812 at stationary hubs 1823, 1825, 1923, 1925.

Figure 27:
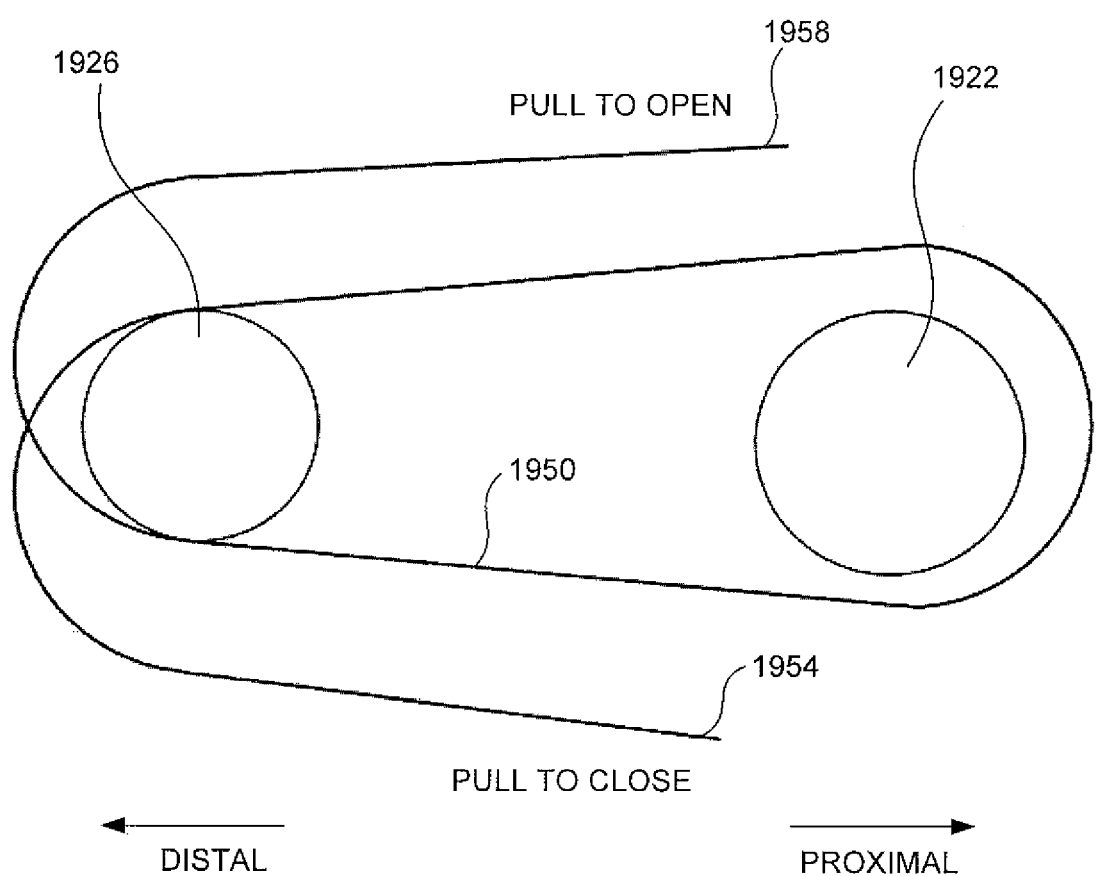
FIG. 27 is a plan view of an example configuration of a cable.

FIG. 27 is a plan view of an exemplary configuration of the cable 1950. The cable 1950 extends from a generally proximal location (e.g., shaft 804), distally around the pulley 1926, proximally around the pulley 1922, distally around the pulley 1926, and towards the generally proximal location. Accordingly, pulling on the cable portion 1954 (e.g., labeled "pull to close") causes counter-clockwise rotation of the pulleys 1922, 1926, which articulates the jaw 1810 in a closing direction. Similarly, pulling on the cable portion 1958 (e.g., labeled "pull to open") causes clockwise rotation of the pulleys 1922, 1926, which articulates the jaw 1810 in an opening direction. The jaw 1808, the pulleys 1822, 1826, the cable 1952, and the cable portions 1956, 1960 operate in a substantially similar manner.

Figure 28:
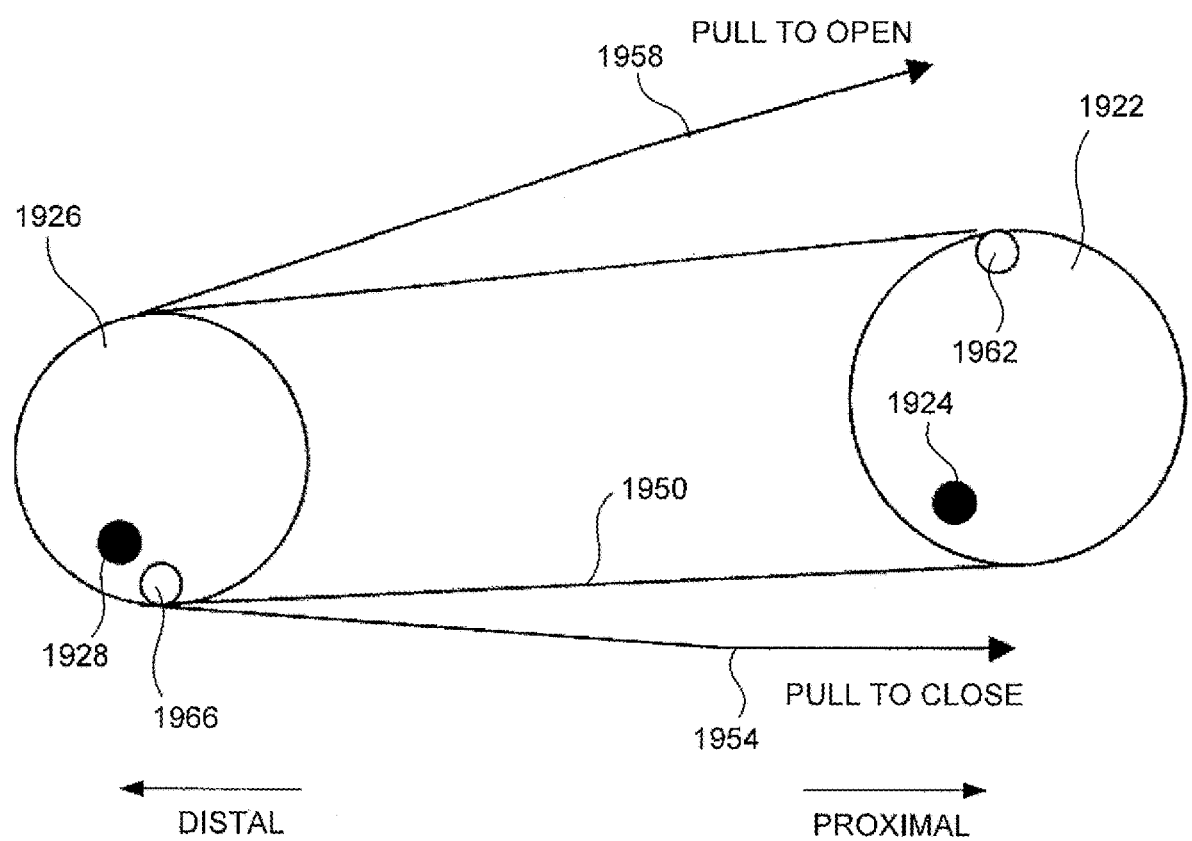
FIG. 28 a plan view of an example configuration of a cable in accordance with at least some aspects of the present disclosure.

FIG. 28 is a plan view of an exemplary configuration of the cable 1950 of FIG. 27 with the cable 1950 tightened and attached to the pulleys 1922, 1926. In this example, the cable 1950 is attached to the pulley 1922, such as at about a 12 o'clock position (e.g., point 1962), and is attached to the pulley 1926, such as at about a 6 o'clock position (e.g., point 1966).

The present disclosure contemplates that cable-driven mechanisms may employ generally similar kinematic concepts and therefore generally similar positions of the pulleys 1822, 1826, 1922, 1926 and the pins 1824, 1828, 1924, 1928 as the gears 822, 826, 922, 926 of some double-gear mechanisms.

Some exemplary cable-driven mechanisms 1813 permit the use of a shortened head 1812 as compared to some double-gear mechanisms 813 because space for proximal and/or distal motion of the rack 832 may not be provided. Some exemplary cable-driven mechanisms 1813 may be less expensive and/or may be constructed with less precision than some double-gear mechanisms 813. Some exemplary cable-driven mechanisms 1813 may be subject to less internal friction than some double-gear mechanisms 813.

Some exemplary cable-driven mechanisms 1813 may be operable using a plurality of linkages 803. For example, a first linkage 803 may be configured to pull on cable portions 1954, 1956 to close the jaws 1808, 1810 and/or a second linkage 803 may be configured to pull on the cable portions 1958, 1960 to open the jaws 1808, 1810. Thus, some exemplary cable-driven mechanisms 1813 may include only linkages 803 for exerting tension as compared to linkages capable of transmitting substantial force in both tension and compression.

Some exemplary clamps may incorporate tip bias to account for the effects of tissue on the angular relationships of the jaws. For example, closing the jaws of an exemplary clamp on tissue may cause the jaws to flex apart due to bending stress. Thus, the angular positions of the jaws when shut on tissue may differ from the angular positions of the jaws when shut empty. Some exemplary embodiments may account for such differences by, for example, constructing the end effector such that the jaws are slightly non-parallel in the opened position when the jaws are empty. For example, the tips of the jaws may be biased inward from parallel by about 0.020 inches in the closed position when empty, which may result in the jaws being substantially parallel in the closed position when tissue is between the jaws. More generally, the design of the end effector and the jaws may be such that the jaws are substantially parallel when actuated on tissue.

As used herein, "substantially parallel" generally means that the jaws are within about +/−5 degrees of parallel. In some detailed exemplary embodiments, substantially parallel may mean that the jaws are within about +/−3 degrees and/or within about +/−0.5 degrees of parallel.

INCORPORATE BY REFERENCE: FORCE-LIMITING, RETURN SPRING, OR LOCK BUTTON FEATURES OF THE HANDLE

While exemplary embodiments have been set forth above for the purpose of disclosure, modifications of the disclosed embodiments as well as other embodiments thereof may occur to those skilled in the art. Accordingly, it is to be understood that the disclosure is not limited to the above precise embodiments and that changes may be made without departing from the scope. For instance, the examples, embodiments, geometries, materials, dimensions, ratios, steps, and the like discussed above are illustrative and are not required. Likewise, it is to be understood that it is not necessary to meet any or all of the stated advantages or objects disclosed herein to fall within the scope of the disclosure, since inherent and/or unforeseen advantages may exist even though they may not have been explicitly discussed herein.

What is claimed is:

1. A surgical clamp, comprising:
an end effector including,
   a head configured to be disposed at a distal end of a shaft,
   a first jaw and a second jaw extending from the head,
   a first rotating offset, the first rotating offset being rotatably mounted to the head, the first rotating offset being pivotably coupled to the first jaw, and
   a second rotating offset, the second rotating offset being rotatably mounted to the head, the second rotating offset being pivotably and slidably coupled to the first jaw;
wherein the first rotating offset and the second rotating offset are configured to articulate the first jaw by rotation of the first rotating offset and the second rotating offset effected by movement of at least one linkage; and
wherein the end effector is configured to move between an open position in which the first jaw and the second jaw are separated and substantially non-parallel, an intermediate position in which the first jaw and the second jaw are separated by a first distance and substantially parallel, and a closed position in which the first jaw and the second jaw are separated by a second distance, less than the first distance, and substantially parallel to one another.

2. The surgical clamp of claim 1, wherein the first rotating offset is pivotably coupled to the first jaw by a first pin.

3. The surgical clamp of claim 1, wherein the second rotating offset is pivotably and slidably coupled to the first jaw by a second pin, the second pin being slidable in a slot.

4. The surgical clamp of claim 3, wherein the slot is disposed in the first jaw; and wherein the second pin is mounted to the second rotating offset.

5. The surgical clamp of claim 1, wherein the first rotating offset comprises a first pulley.

6. The surgical clamp of claim 1, wherein the second rotating offset comprises a second pulley.

7. The surgical clamp of claim 1, further comprising the shaft, the shaft including a proximal end and the distal end, the at least one linkage extending along the shaft.

8. The surgical clamp of claim 7, further comprising a handle disposed at the proximal end of the shaft, the handle including an actuator operatively connected to the end effector by the at least one linkage.

9. The surgical clamp of claim 1, wherein the at least one linkage comprises at least one of a band, a rod, a cable, a rope, and a chain.

10. A surgical clamp, comprising:
an end effector including,
   a head configured to be disposed at a distal end of a shaft,
   a first jaw and a second jaw extending from the head,
   a first rotating offset comprising a first pulley, the first rotating offset being rotatably mounted to the head, the first rotating offset being pivotably coupled to the first jaw by a first pin, and
   a second rotating offset comprising a second pulley, the second rotating offset being rotatably mounted to the head, the second rotating offset being pivotably and slidably coupled to the first jaw by a second pin mounted to the second rotating offset, the second pin being slidable in a slot disposed in the first jaw;
wherein the first rotating offset and the second rotating offset are configured to articulate the first jaw by rotation of the first rotating offset and the second rotating offset effected by movement of at least one linkage; and
wherein the end effector is configured to move between an open position in which the first jaw and the second jaw are separated and substantially non-parallel, an intermediate position in which the first jaw and the second jaw are separated by a first distance and substantially parallel, and a closed position in which the first jaw and the second jaw are separated by a second distance, less than the first distance, and substantially parallel to one another.

11. The surgical clamp of claim 10, wherein the at least one linkage comprises at least one rope.

12. A method of operating a surgical device comprising an end effector including a head, a first jaw, and a second jaw, the first jaw and the second jaw coupled to and extending from the head, the method comprising:
   repositioning the first jaw from an open position in which the first jaw and the second jaw are separated and substantially non-parallel to an intermediate position in which the first jaw and the second jaw are separated by a first distance and substantially parallel, and to a closed position in which the first jaw and the second jaw are separated by a second distance, less than the first distance, and substantially parallel to one another, where repositioning the first jaw comprises,
      rotating a first rotating offset rotatably mounted to the head, the first rotating offset being pivotably coupled to the first jaw, and
      rotating a second rotating offset rotatably mounted to the head, the second rotating offset being pivotably and slidably coupled to the first jaw.

13. The method of claim 12, wherein:
the first rotating offset is pivotably coupled to the first jaw by a first pin; and
rotating the first rotating offset comprises rotating the first jaw relative to the first rotating offset about the first pin.

14. The method of claim 12, wherein:
the second rotating offset is pivotably and slidably coupled to the first jaw by a second pin slidably disposed in a slot; and
rotating the second rotating offset comprises rotating the first jaw relative to the second rotating offset and translating the first jaw relative to the second rotating offset.

15. The method of 14, wherein:
rotating the first jaw relative to the second rotating offset comprises rotating the first jaw relative to the second rotating offset about the second pin; and
translating the first jaw relative to the second rotating offset comprises translating the second pin relative to the slot.

16. The method of claim 12, wherein:
the first rotating offset comprises a first pulley;
the second rotating offset comprises a second pulley;
rotating the first rotating offset comprises rotating the first pulley; and
rotating the second rotating offset comprises rotating the second pulley.

17. The method of claim 12, further comprising repositioning the second jaw from the open position, to the intermediate position, and to the closed position.

18. A surgical clamp, comprising:
an end effector including,
a first jaw including a first sliding pin slot and a first rotating pin cavity,
a second jaw including a second sliding pin slot and a second rotating pin cavity,
a first rotating offset comprising a first pulley, the first rotating offset being mounted to a head, the first rotating offset being pivotably and slidably coupled to the first jaw by a first pin received within the first sliding pin slot, and
a second rotating offset comprising a second pulley, the second rotating offset being mounted to the head, the second rotating offset being pivotably and slidably coupled to the second jaw by a second pin mounted to the second rotating offset, the second pin received within the second sliding pin slot;
wherein the first rotating offset and the second rotating offset are configured to articulate the first jaw and the second jaw by rotation of the first rotating offset and the second rotating offset effected by movement of at least one linkage; and
wherein the end effector is configured to move between an open position in which the first jaw and the second jaw are separated and substantially non-parallel, an intermediate position in which the first jaw and the second jaw are separated by a first distance and substantially parallel, and a closed position in which the first jaw and the second jaw are separated by a second distance, less than the first distance, and substantially parallel to one another.

19. An end effector, comprising:
a first wheel rotatable about a first axis, the first wheel including a first pin radially spaced from the first axis and parallel to the first axis;
a second wheel rotatable about a second axis, the second wheel including a second pin radially spaced from the second axis and parallel to the second axis;
a first jaw defining a first hole and a first slot, the first pin of the first wheel received in the first slot of the first jaw;
a second jaw defining a second hole and a second slot, the second pin of the second wheel received in the second slot of the second jaw,
wherein the first and second jaws are movable relative to one another between a first open non-parallel state, a second open parallel state, and a third closed parallel state in response to rotation of at least one of the first and second wheels.

* * * * *